(12) United States Patent
Saijo

(10) Patent No.: US 10,835,342 B2
(45) Date of Patent: Nov. 17, 2020

(54) MEDICAL OBSERVATION APPARATUS AND CONTROL METHOD

(71) Applicant: Sony Olympus Medical Solutions Inc., Tokyo (JP)

(72) Inventor: Hiroki Saijo, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 72 days.

(21) Appl. No.: 15/897,174

(22) Filed: Feb. 15, 2018

(65) Prior Publication Data

US 2018/0250092 A1  Sep. 6, 2018

(30) Foreign Application Priority Data

Mar. 2, 2017  (JP) ................. 2017-039402

(51) Int. Cl.
| | |
|---|---|
| A61B 90/25 | (2016.01) |
| A61B 90/00 | (2016.01) |
| A61B 90/50 | (2016.01) |
| G02B 21/36 | (2006.01) |
| G02B 21/00 | (2006.01) |
| G02B 21/24 | (2006.01) |

(52) U.S. Cl.
CPC ............ *A61B 90/25* (2016.02); *A61B 90/361* (2016.02); *A61B 90/50* (2016.02); *G02B 21/0012* (2013.01); *G02B 21/24* (2013.01); *G02B 21/362* (2013.01); *G02B 21/365* (2013.01); *A61B 2090/373* (2016.02); *A61B 2090/508* (2016.02); *G02B 21/368* (2013.01)

(58) Field of Classification Search
CPC ........ A61B 2090/373; A61B 2090/508; A61B 90/25; A61B 90/361; A61B 90/50; G02B 21/0012; G02B 21/24; G02B 21/362; G02B 21/365; G02B 21/368

See application file for complete search history.

(56) References Cited

U.S. PATENT DOCUMENTS

| | | | | |
|---|---|---|---|---|
| 4,021,825 A | * | 5/1977 | McCann ............. | G02B 21/362 396/432 |
| 5,223,877 A | * | 6/1993 | Kawasaki ............... | G03B 7/20 348/E5.044 |
| 5,420,716 A | * | 5/1995 | Fukaya .................. | G02B 7/001 359/368 |
| 5,552,929 A | * | 9/1996 | Fukaya .................. | G02B 21/18 359/380 |
| 5,601,549 A | * | 2/1997 | Miyagi ............. | A61B 1/00193 606/4 |

(Continued)

FOREIGN PATENT DOCUMENTS

JP  2016-42982  4/2016

*Primary Examiner* — Peter D Le

(74) *Attorney, Agent, or Firm* — Xsensus, LLP

(57) ABSTRACT

There is provided a medical observation apparatus including: a control section configured to control, on a basis of a predetermined operation related to a movement of an imaging field of view, the movement of the imaging field of view in an imaging device supported by an arm including a plurality of links joined to each other by joint sections. The control section controls the movement of the imaging field of view by performing a cropping range control that crops an imaging range of the imaging device on the basis of the predetermined operation.

20 Claims, 8 Drawing Sheets

(56) References Cited

U.S. PATENT DOCUMENTS

| | | | | |
|---|---|---|---|---|
| 5,631,697 A * | 5/1997 | Nishimura | G01S 3/7865 | 348/170 |
| 5,650,819 A * | 7/1997 | Sato | H04N 5/23212 | 348/240.99 |
| 5,701,157 A * | 12/1997 | Kato | H04N 5/232 | 348/240.99 |
| 5,748,366 A * | 5/1998 | Yasunaga | G02B 21/0012 | 359/363 |
| 5,836,869 A * | 11/1998 | Kudo | A61B 1/00039 | 600/173 |
| 6,434,416 B1 * | 8/2002 | Mizoguchi | G02B 21/0012 | 600/427 |
| 6,661,571 B1 * | 12/2003 | Shioda | A61B 1/04 | 359/368 |
| 7,860,614 B1 * | 12/2010 | Reger | B25J 9/1671 | 700/10 |
| 2001/0055150 A1 * | 12/2001 | Ito | A61B 90/25 | 359/363 |
| 2003/0069471 A1 * | 4/2003 | Nakanishi | A61B 1/0005 | 600/101 |
| 2004/0246469 A1 * | 12/2004 | Hirose | A61B 1/00048 | 356/139.03 |
| 2005/0228257 A1 * | 10/2005 | Ishikawa | G02B 21/0012 | 600/407 |
| 2006/0023324 A1 * | 2/2006 | Otsuka | F16M 11/10 | 359/871 |
| 2007/0025714 A1 * | 2/2007 | Shiraki | G03B 13/36 | 396/72 |
| 2009/0062604 A1 * | 3/2009 | Minosawa | A61B 1/00096 | 600/104 |
| 2009/0190209 A1 * | 7/2009 | Nakamura | G02B 21/0012 | 359/375 |
| 2009/0192524 A1 * | 7/2009 | Itkowitz | B25J 9/1666 | 606/130 |
| 2009/0245600 A1 * | 10/2009 | Hoffman | A61B 1/00039 | 382/128 |
| 2009/0326556 A1 * | 12/2009 | Diolaiti | A61B 1/00009 | 606/130 |
| 2010/0036199 A1 * | 2/2010 | Karasawa | A61B 1/00085 | 600/109 |
| 2010/0274078 A1 * | 10/2010 | Kim | A61B 1/00149 | 600/102 |
| 2011/0273549 A1 * | 11/2011 | Kase | A61B 1/00147 | 348/68 |
| 2011/0301758 A1 * | 12/2011 | Nakajima | B25J 9/1633 | 700/259 |
| 2011/0304749 A1 * | 12/2011 | Ishikawa | H04N 5/23219 | 348/240.1 |
| 2012/0143353 A1 * | 6/2012 | Kishi | B25J 3/04 | 700/3 |
| 2012/0281106 A1 * | 11/2012 | Foster | H04N 5/23254 | 348/222.1 |
| 2013/0010081 A1 * | 1/2013 | Tenney | A61B 34/30 | 348/47 |
| 2014/0051921 A1 * | 2/2014 | Miller | A61B 1/00009 | 600/103 |
| 2014/0294370 A1 * | 10/2014 | Lin | H04N 5/23258 | 396/53 |
| 2015/0305603 A1 * | 10/2015 | Gal | A61B 1/00167 | 600/103 |
| 2015/0327765 A1 * | 11/2015 | Crane | A61B 5/0059 | 348/77 |

\* cited by examiner

FIG. 10
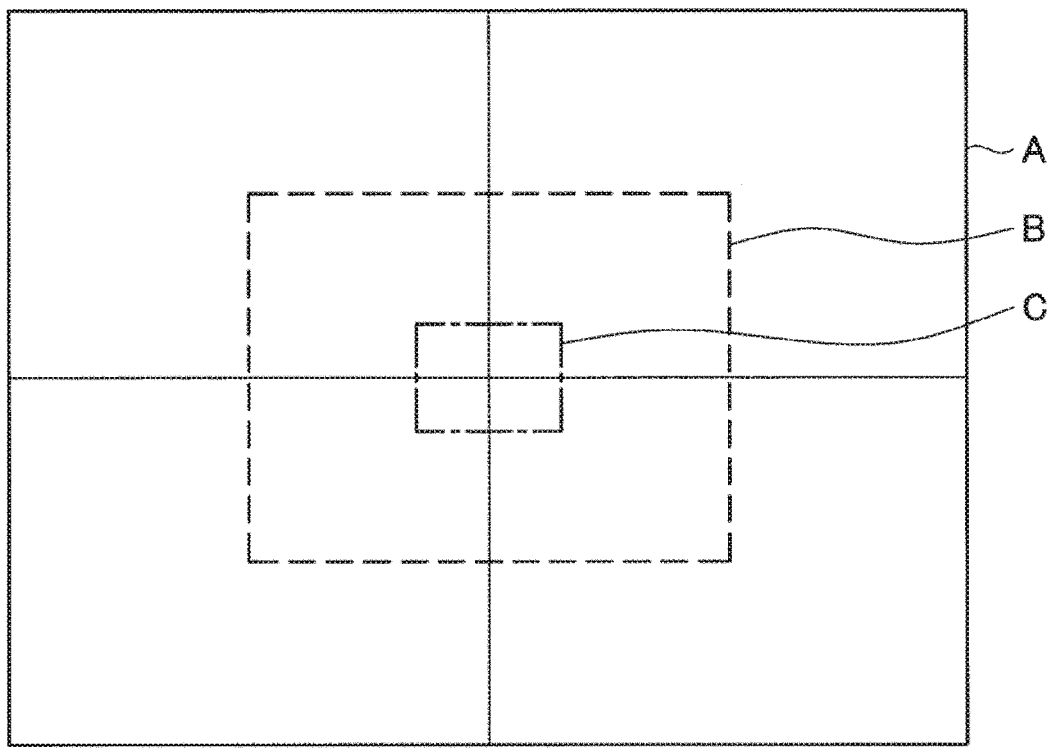
 IMAGING RANGE OF IMAGING DEVICE (IMAGING RANGE OF IMAGE SENSOR)
 MOVABLE RANGE OF CENTER POSITION OF ELECTRONIC FIELD OF VIEW MOVEMENT
 RANGE IN WHICH CENTER RETURN OF CENTER POSITION AFTER MOVEMENT OF ELECTRONIC FIELD OF VIEW MOVEMENT IS UNNECESSARY

MEDICAL OBSERVATION APPARATUS AND CONTROL METHOD

CROSS REFERENCE TO RELATED APPLICATIONS

This application claims the benefit of Japanese Priority Patent Application JP 2017-039402 filed Mar. 2, 2017, the entire contents of which are incorporated herein by reference.

BACKGROUND

The present disclosure relates to a medical observation apparatus and a control method.

Recently, in the medical field, to support surgeries, medical observation apparatus capable of enlarged observation of an observation target such as an affected area are used in some cases. Examples of medical observation apparatus include a medical observation apparatus provided with an optical microscope, and a medical observation apparatus provided with an imaging device that functions as an electronic imaging microscope. In the following, the above medical observation apparatus provided with an optical microscope will be designated an "optical medical observation apparatus". Also, in the following, the above medical observation apparatus provided with an imaging device will be designated an "electronic imaging medical observation apparatus" or simply a "medical observation apparatus" in some cases.

With an electronic imaging medical observation apparatus, along with the increased image quality of imaging devices, the increased image quality of display devices on which taken images are displayed, and the like, the same or higher image quality than an optical medical observation apparatus has come to be obtained. Also, because a user who uses an electronic imaging medical observation apparatus (for example, medical personnel such as a surgeon or a surgeon's assistant) is not required to peer into an eyepiece lens included in an optical microscope like in the case of using an optical medical observation apparatus, it is possible to move the position of the imaging device more freely.

In such circumstances, technologies related to electronic imaging medical observation apparatus are being developed. Examples of the above technologies include the technology described in JP 2016-42982A.

SUMMARY

With an electronic imaging medical observation apparatus, the imaging device is supported by an arm. Also, in a medical observation apparatus, for example, by having a user who uses the medical observation apparatus manually move the arm that supports the imaging device, or by having a movement mechanism capable of moving the arm operate on the basis of an operation performed by the user on an operating device such as a footswitch, the imaging field of view in the imaging devices moves. Hereinafter, a user who uses the medical observation apparatus will be simply designated the "user" in some cases.

Herein, in the case in which the user manually moves the imaging field of view, fine adjustment of the imaging field of view is difficult.

On the other hand, in the case in which the imaging field of view moves by the operation of a movement mechanism, actuators or the like included in the movement mechanism mechanically operate in accordance with operations performed by the user on an operating device such as a footswitch. Thus, in the case in which the imaging field of view moves by the operation of the movement mechanism, the user is able to make fine adjustments of the imaging field of view more easily than in the case of manually moving the imaging field of view.

However, in the case in which the imaging field of view moves by the mechanical operation of the movement mechanism, backlash causes a certain degree of wait time to occur from when the user operates the operating device until the imaging field of view moves. Also, there is a risk that the occurrence of a wait time like the above could lead to lowered user convenience.

The present disclosure proposes a new and improved medical observation apparatus and control method capable of making an improvement in convenience.

According to an embodiment of the present disclosure, there is provided a medical observation apparatus including: a control section configured to control, on a basis of a predetermined operation related to a movement of an imaging field of view, the movement of the imaging field of view in an imaging device supported by an arm including a plurality of links joined to each other by joint sections. The control section controls the movement of the imaging field of view by performing a cropping range control that crops an imaging range of the imaging device on the basis of the predetermined operation.

In addition, according to an embodiment of the present disclosure, there is provided a control method executed by a medical observation apparatus, the method including: controlling, on a basis of a predetermined operation related to a movement of an imaging field of view, the movement of the imaging field of view in an imaging device supported by an arm including a plurality of links joined to each other by joint sections. In the controlling, the movement of the imaging field of view is controlled by performing a cropping range control that crops an imaging range of the imaging device on the basis of the predetermined operation.

According to an embodiment of the present disclosure, an improvement in convenience can be made.

Note that the effects described above are not necessarily limitative. With or in the place of the above effects, there may be achieved any one of the effects described in this specification or other effects that may be grasped from this specification.

BRIEF DESCRIPTION OF THE DRAWINGS

FIG. 10 is an explanatory diagram for describing an example of a notification-related process related to the control method according to the present embodiment.

DETAILED DESCRIPTION OF THE EMBODIMENT(S)

Figure 1:
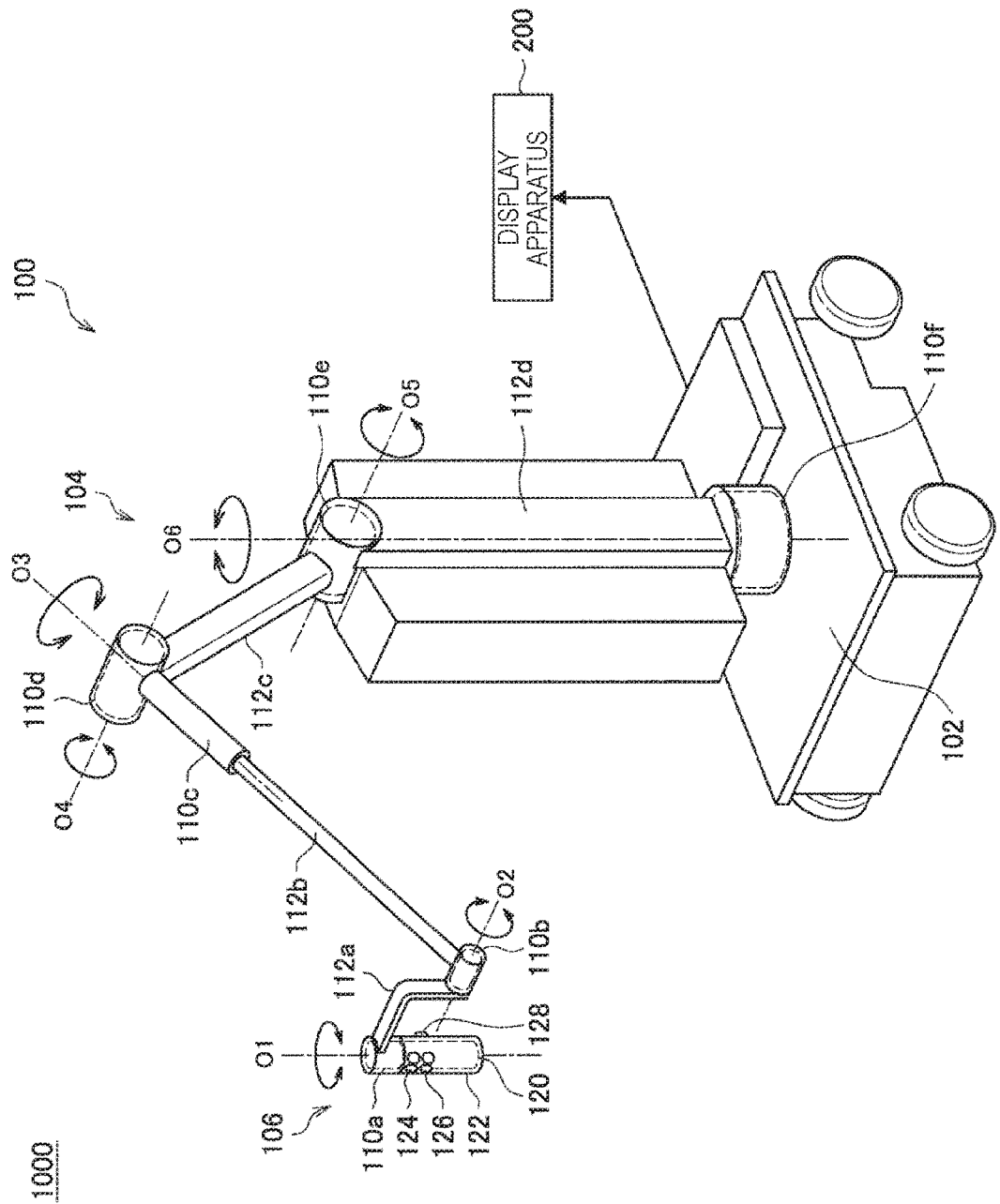
FIG. 1 is an explanatory diagram illustrating an example of a configuration of a medical observation system according to the present embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

The description hereinafter will proceed in the following order.

1. Medical observation system according to present embodiment and control method according to present embodiment 2. Program according to present embodiment (Medical Observation System According to Present Embodiment and Control Method According to Present Embodiment)

Hereinafter, an example of a medical observation system according to the present embodiment will be described, while a control method according to the present embodiment will also be described.

[1] Configuration of Medical Observation System

FIG. 1 is an explanatory diagram illustrating an example of the configuration of a medical observation system 1000 according to the present embodiment. The medical observation system 1000 includes a medical observation apparatus 100 and a display apparatus 200, for example.

Note that the medical observation system according to the present embodiment is not limited to the example illustrated in FIG. 1.

For example, the medical observation system according to the present embodiment additionally may include a control apparatus (not illustrated) that controls various operations in the medical observation apparatus 100. In the medical observation system 1000 illustrated in FIG. 1, as described later, an example is illustrated in which, by providing the medical observation apparatus 100 with a control section (described later) that performs processes according to the control method according to the present embodiment, the medical observation apparatus 100 includes the functions of the control apparatus (not illustrated).

Examples of the control apparatus (not illustrated) include arbitrary equipment capable of performing processes according to the control method according to the present embodiment, such as a "medical controller" and a "computer such as a server". Also, the control apparatus (not illustrated) may be, for example, an integrated circuit (IC) that can be embedded in equipment like the above.

Additionally, the medical observation system according to the present embodiment may also be a configuration that includes multiple medical observation apparatuses 100 and display apparatuses 200. In the case of including multiple medical observation apparatuses 100, in each medical observation apparatus 100, processes according to the control method in the medical observation apparatus 100 described later are performed. Also, in the case in which the medical observation system according to the present embodiment is a configuration that includes multiple medical observation apparatuses 100 and display apparatuses 200, the medical observation apparatus 100 and the display apparatus 200 may be associated in a 1-to-1 manner, or multiple medical observation apparatuses 100 may be associated with a single display apparatus 200. In the case in which multiple medical observation apparatuses 100 are associated with a single display apparatus 200, which medical observation apparatus 100 provides a taken image to be displayed on a display screen is switched by performing a switching operation or the like in the display apparatus 200, for example.

[1-1] Display Apparatus 200

The display apparatus 200 is a display device in the medical observation system 1000, and corresponds to an external display device from the perspective of the medical observation apparatus 100. The display apparatus 200 displays various images on a display screen, such as a taken image (a moving image or multiple still images; the same applies hereinafter) taken in the medical observation apparatus 100, or an image related to a user interface (UI), for example. In addition, the display apparatus 200 may also be a configuration capable of 3D display. The display on the display apparatus 200 is controlled by, for example, the medical observation apparatus 100 or the control apparatus (not illustrated).

In the medical observation system 1000, the display apparatus 200 is installed in an arbitrary location visible to a person involved in a surgery inside an operating room, such as on a wall, the ceiling, or the floor of the operating room, for example. Examples of the display apparatus 200 include a liquid crystal display, an organic EL display, a cathode ray tube (CRT) display, and the like.

Note that the display apparatus 200 is not limited to the example illustrated above.

For example, the display apparatus 200 may also be an arbitrary wearable apparatus that is used by being worn on the body of the surgeon or the like, such as a head-mounted display, an eyewear-type apparatus, or the like.

[1-2] Medical Observation Apparatus 100

The medical observation apparatus 100 is an electronic imaging medical observation apparatus. For example, in the case in which the medical observation apparatus 100 is used during surgery, the surgeon (one example of the user of the medical observation apparatus 100) observes an operating site while referring to a taken image which has been taken by the medical observation apparatus 100 and displayed on the display screen of the display apparatus 200, and performs various treatments, such as techniques depending on the surgical procedure, on the operating site.

First, FIG. 1 will be referenced to describe an example of a hardware configuration of the medical observation apparatus 100.

The medical observation apparatus 100 is provided with a base 102, an arm 104, and an imaging device 106, for example.

Additionally, although not illustrated in FIG. 1, the medical observation apparatus 100 may also be provided with, for example, one or multiple processors (not illustrated) including a computational circuit such as a microprocessing unit (MPU), read-only memory (ROM; not illustrated), random access memory (RAM; not illustrated), a recording medium (not illustrated), and a communication device (not illustrated). The medical observation apparatus 100 runs on electric power supplied from an internal power source such as a battery provided in the medical observation apparatus 100, on electric power supplied from a connected external power source, or the like, for example.

The one or multiple processors (not illustrated) function as the control section described later. The ROM (not illustrated) stores programs and control data such as computational parameters used by the one or multiple processors (not illustrated). The RAM (not illustrated) temporarily stores programs executed by the one or multiple processors (not illustrated), or the like.

The recording medium (not illustrated) is a storage device provided in the medical observation apparatus 100, and stores various data, such as information indicating a target field of view movement velocity described later or other data related to the control method according to the present embodiment, various applications, and the like, for example. Herein, examples of the recording medium (not illustrated) include a magnetic recording medium such as a hard disk, non-volatile memory such as flash memory, and the like. Additionally, the recording medium (not illustrated) may also be removable from the medical observation apparatus 100.

The communication device (not illustrated) is a communication device provided in the medical observation apparatus 100, and fulfills a role of communicating in a wireless or wired manner with an external apparatus such as the display apparatus 200. Herein, examples of the communication device (not illustrated) include an IEEE 802.15.1 port and transmitting-receiving circuit (wireless communication), an IEEE 802.11 port and transmitting-receiving circuit (wireless communication), a communication antenna and a radio frequency (RF) circuit (wireless communication), a local area network (LAN) terminal and a transmitting-receiving circuit (wired communication), and the like.

[1-2-1] Base 102

The base 102 is the base of the medical observation apparatus 100. One end of the arm 104 is connected to the base 102, and the base 102 supports the arm 104 and the imaging device 106.

Also, casters are provided on the base 102, for example, and the medical observation apparatus 100 contacts the floor through the casters. By providing the casters, the medical observation apparatus 100 is able to move easily over the floor by the casters.

[1-2-2] Arm 104

The arm 104 includes multiple links joined to each other by joint sections.

In addition, the arm 104 supports the imaging device 106. The imaging device 106 supported by the arm 104 is movable three-dimensionally, and after moving, the position and the attitude of the imaging device 106 are maintained by the arm 104. By having the imaging device 106 supported by the arm 104 move three-dimensionally, in the medical observation apparatus 100, the imaging field of view of the imaging device 106 moves in a user-desired direction.

More specifically, the arm 104 includes, for example, multiple joint sections 110a, 110b, 110c, 110d, 110e, and 110f, and multiple links 112a, 112b, 112c, and 112d rotatably joined to each other by the joint sections 110a, 110b, 110c, 110d, and 110e. In other words, in the medical observation apparatus 100 illustrated in FIG. 1, six degrees of freedom are realized in relation to the movement of the imaging device 106 by six rotation axes (first axis O1, second axis O2, third axis O3, fourth axis O4, fifth axis O5, and sixth axis O6) corresponding to the six joint sections 110a, 110b, 110c, 110d, 110e, and 110f included in the arm 104.

The link 112a is an approximately L-shaped member, while each of the links 112b, 112c, and 112d is an approximately rod-shaped member. One end of the link 112d is joined to the base 102 through the joint section 110f, while the other end of the link 112d is joined to one end of the link 112c through the joint section 110e. Also, the other end of the link 112c is joined to one end of the link 112b through the joint sections 110d and 110c. Also, the other end of the link 112b is joined to one end of the link 112a through the joint section 110b, while the other end of the link 112a and the imaging device 106 are joined through the joint section 110a.

As illustrated in FIG. 1, with the base 102 acting as a fulcrum, the ends of each of the multiple links 112a, 112b, 112c, and 112d are rotatably joined to each other by joint sections 110a, 110b, 110c, 110d, and 110e, thereby configuring the arm 104 in an arm shape extending from the base 102.

Actuators (not illustrated) are provided in each of the joint sections 110a, 110b, 110c, 110d, and 110e. Each of the joint sections 110a, 110b, 110c, 110d, and 110e rotates about the corresponding rotation axis by the driving of the actuators (not illustrated). The driving of the actuators (not illustrated) is controlled by, for example, a processor that functions as the control section described later, or an external control apparatus (not illustrated).

By having each of the joint sections 110a, 110b, 110c, 110d, and 110e rotate about the corresponding rotation axis by the driving of the actuators (not illustrated), operations of the arm 104, such as extending and contracting (folding up) the arm 104, for example, are realized.

To give one example, by controlling rotation about the first axis O1, rotation about the optical axis of the imaging device 106 is controlled. Also, by controlling each of rotation about the second axis O2 and rotation about the third axis O3, the direction of the optical axis of the imaging device 106 with respect to the horizontal plane is controlled. In other words, the first axis O1, the second axis O2, and the third axis O3 on the front end side of the arm 104 (that is, the side opposite the side joined to the base 102) may be considered to be the rotation axes that primarily control the attitude (the direction of the optical axis) of the imaging device 106. In the medical observation apparatus 100, for example, by controlling the rotation of the joint sections 110a, 110b, and 110c corresponding to the first axis O1, the second axis O2, and the third axis O3, primarily the attitude of the imaging device 106 is controlled.

Also, to give another example, by controlling rotation about the fourth axis O4, rotation about the fifth axis O5, and rotation about the sixth axis O6, the three-dimensional position of the imaging device 106 is controlled. In the medical observation apparatus 100, for example, by controlling the rotation of the joint sections 110d, 110e, and 110f corresponding to the fourth axis O4, the fifth axis O5, and the sixth axis O6 on the root side of the arm 104 (that is, the side joined to the base 102), primarily the position of the imaging device 106 is controlled.

For example, by having the arm 104 operate as above, the imaging device 106 supported by the arm 104 moves three-dimensionally. Also, as described above, by having the imaging device 106 supported by the arm 104 move three-dimensionally, the imaging field of view of the imaging device 106 moves.

In other words, the mechanism of the arm 104 provided with actuators (not illustrated), such as the one illustrated with reference to FIG. 1, for example, corresponds to an example of the movement mechanism according to the present embodiment, in which the movement mechanism moves the arm 104 to cause the imaging field of view in the imaging device 106 to move.

However, the configuration of the movement mechanism according to the present embodiment is not limited to the example illustrated with reference to FIG. 1. For example, the movement mechanism according to the present embodiment may be an arbitrary configuration capable of moving the arm 104 to change the position and the attitude of the imaging device 106, while also maintaining the position and the attitude of the imaging device 106 with the arm 104.

[1-2-3] Imaging Device 106

The imaging device 106 is supported by the arm 104, and images an observation target such as an operating site of a patient, for example. Imaging in the imaging device 106 is controlled by, for example, a processor that functions as the control section described later, or an external control apparatus (not illustrated).

The imaging device 106 has a configuration corresponding to an electronic imaging microscope, for example.

More specifically, for example, the imaging device 106 includes an imaging member 120 and a barrel member 122 having an approximately cylindrical shape, with the imaging member 120 being provided inside the barrel member 122.

For example, the imaging member 120 includes an optical system and an imaging element. The optical system includes optical elements such as a mirror and one or multiple lenses, such as an objective lens, a zoom lens, and a focus lens. The imaging element takes an image of an observation target with light transmitted through the optical system.

On an aperture on the bottom end of the barrel member 122 (the lower end in FIG. 1), for example, a cover glass for protecting the imaging member 120 is provided.

Additionally, for example, a light source is provided inside the barrel unit 122, and during imaging, the subject is irradiated with illuminating light radiating from the light source through the cover glass. Reflected light (observation light) from the subject irradiated with illuminating light enters the imaging member 120 through the cover glass, whereby an image signal indicating the subject (an image signal indicating a taken image) is obtained by the imaging member 120.

As the imaging member 120, any of various known types of configurations used in an electronic imaging microscope section can be applied.

To give one example, the imaging member 120 includes an optical system, and an image sensor using multiple imaging elements, such as a complementary metal-oxide semiconductor (CMOS) or a charge-coupled device (CCD). The imaging member 120 may also include a pair of imaging elements, or in other words, be configured to function as what is called a stereo camera. The imaging member 120 is equipped with one or multiple functions typically provided in an electronic imaging microscope section, including at least a zoom function (one or both of an optical zoom function and an electronic zoom function), such as an autofocus (AF) function.

In addition, the imaging member 120 may also be configured to be capable of imaging at what are called high resolutions, such as 4K and 8K, for example. By configuring the imaging member 120 to be capable of imaging at high resolutions, it becomes possible to ensure a predetermined resolution (such as full HD image quality, for example), while also displaying an image on the display apparatus 200 having a large display screen, such as 50 inches or more, for example. For this reason, visibility is improved for the surgeon watching the display screen. Also, by configuring the imaging member 120 to be capable of imaging at high resolutions, even if the taken image is enlarged by the electronic zoom function and displayed on the display screen of the display apparatus 200, it is still possible to ensure a predetermined resolution. Furthermore, in the case of using the electronic zoom function to ensure a predetermined resolution, since it is possible to reduce the performance of the optical zoom function in the imaging device 106, the optical system of the imaging device 106 can be simplified, and the imaging device 106 can be configured more compactly.

In the imaging device 106, for example, various operating devices for controlling the operation of the imaging device 106 are provided. For example, in FIG. 1, a zoom switch 124, a focus switch 126, and an operating mode change switch 128 are provided on the imaging device 106. Note that the positions and shapes in which to provide the zoom switch 124, the focus switch 126, and the operating mode change switch 128 obviously are not limited to the example illustrated in FIG. 1.

The zoom switch 124 and the focus switch 126 are an example of an operating device for adjusting the imaging parameters in the imaging device 106. By performing an operation on the zoom switch 124, the zoom magnification is adjusted, and the zoom is adjusted. Also, by performing an operation on the focus switch 126, the focal length is adjusted, and the focus is adjusted. An operations on the zoom switch 124 corresponds to a zoom-related operation described later.

The operating mode change switch 128 is an example of an operating device for changing the operating mode of the arm 104 in the imaging device 106. By performing an operation on the operating mode change switch 128, the operating mode of the arm 104 is changed. Examples of operating modes of the arm 104 include a locked mode and a free mode.

Herein, the locked mode according to the present embodiment is, for example, an operating mode in which the position and the attitude of the imaging device 106 are locked by using brakes to restrain rotation about each rotation axis provided in the arm 104. In other words, in the locked mode, the position and the attitude of the imaging device 106 are maintained, and the imaging field of view in the imaging device 106 is locked.

Also, the free mode according to the present embodiment is an operating mode in which the above brakes are released, thereby allowing each rotation axis provided in the arm 104 to rotate freely.

For example, in the free mode, the position and the attitude of the imaging device 106 are adjustable by direct operations performed by the surgeon. Herein, a direct operation according to the present embodiment means, for example, an operation in which the surgeon grips the imaging device 106 with his or her hand, and directly moves the imaging device 106.

Also, in the free mode, for example, it is possible to adjust the position and the attitude of the imaging device 106 by having the movement mechanism operate on the basis of an operation performed by the user with respect to an operating device external to the medical observation apparatus 100, such as a footswitch, or an operation performed by the user with respect to an operating device such as a switch provided on the medical observation apparatus 100.

In other words, in the free mode, the imaging field of view in the imaging device 106 moves because the user moves the arm 104 manually, or because the movement mechanism operates on the basis of an operation performed by the user with respect to an operating device.

One example of an operation with respect to the operating mode change switch 128 is an operation of pressing the operating mode change switch 128. For example, the operating mode of the arm 104 becomes the free mode while the surgeon is pressing the operating mode change switch 128, and the operating mode of the arm 104 becomes the locked mode when the surgeon is not pressing the operating mode change switch 128.

The image signal (image data) generated by imaging in the imaging device 106 is subjected to image processing in a processor that functions as the control section described later, for example. Examples of image processing according to the present embodiment include one or multiple processes from among various processes such as gamma correction, white balance adjustment, image enlargement or reduction related to the electronic zoom function, and pixel interpolation, for example. Note that in the case in which the medical observation system according to the present embodiment includes a control apparatus (not illustrated) that controls various operations in the medical observation apparatus 100, the image processing according to the present embodiment may also be performed in the control apparatus (not illustrated).

For example, the medical observation apparatus 100 transmits a display control signal and the image signal subjected to imaging processing as above to the display apparatus 200. By transmitting the display control signal and the image signal to the display apparatus 200, on the display screen of the display apparatus 200, a taken image in which the observation target is imaged (for example, a taken image in which the operating site is imaged) is displayed enlarged or reduced at a desired magnification by one or both of the optical zoom function and the electronic zoom function.

The medical observation apparatus 100 includes the hardware configuration illustrated with reference to FIG. 1, for example.

Note that the hardware configuration of the medical observation apparatus according to the present embodiment is not limited to the configuration illustrated with reference to FIG. 1.

For example, the medical observation apparatus according to the present embodiment may also be a configuration not provided with the base 102, in which the arm 104 is directly attached to the ceiling, a wall, or the like of the operating room or the like. For example, in the case in which the arm 104 is attached to the ceiling, the medical observation apparatus according to the present embodiment becomes a configuration in which the arm 104 hangs down from the ceiling.

Also, although FIG. 1 illustrates an example configured so that six degrees of freedom are realized with respect to the driving of the imaging device 106, the configuration of the arm 104 is not limited to a configuration whereby the degrees of freedom with respect to the driving of the imaging device 106 become six degrees of freedom. For example, it is sufficient to configure the arm 104 so that the imaging device 106 can move appropriately in accordance with the application, and factors such as the number and arrangement of joint sections and links, and the directions of the drive shafts of the joint sections can be set appropriately so that the arm 104 has the desired degrees of freedom.

Also, although FIG. 1 illustrates an example in which various types of operating devices for controlling the operation of the imaging device 106 are provided on the imaging device 106, some or all of the operating devices illustrated in FIG. 1 may also not be provided on the imaging device 106. To give one example, the various types of operating devices for controlling the operation of the imaging device 106 may also be provided in another part other than the imaging device 106 included in the medical observation apparatus according to the present embodiment. Also, to give another example, the various types of operating devices for controlling the operation of the imaging device 106 may also be external operating devices, such as a footswitch or a remote controller.

Also, although FIG. 1 illustrates the barrel member 122 of the imaging device 106 are a simple cylindrical shape for the sake of simplicity, a grip member gripped by the surgeon may be provided on the barrel member 122. Examples of the grip member include members with arbitrary shapes that can be gripped by the surgeon, such as a member with a handle structure that can be gripped by the surgeon.

Figure 2:
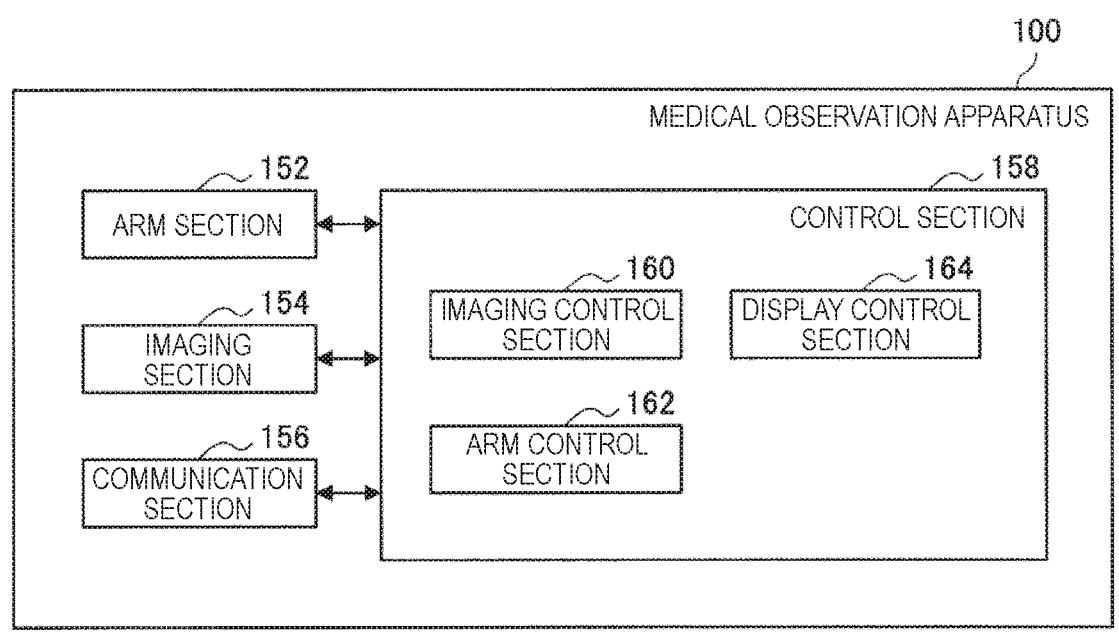
FIG. 2 is a function block diagram illustrating an example of a configuration of a medical observation apparatus according to the present embodiment.

Next, the medical observation apparatus 100 illustrated in FIG. 1 will be described using function blocks. FIG. 2 is a function block diagram illustrating an example of the configuration of the medical observation apparatus 100 according to the present embodiment.

For example, the medical observation apparatus 100 is provided with an arm section 152, an imaging section 154, a communication section 156, and a control section 158.

The arm section 152 includes the arm 104, and supports the imaging device 106 included in the imaging section 154. Also, as illustrated with reference to FIG. 1, the arm 104 included in the arm section 152 is provided with, for example, a movement mechanism that moves the arm 104 to cause the imaging field of view of the imaging device 106 to move.

The imaging section 154 includes the imaging device 106, and images an observation target. Imaging in the imaging section 154 is controlled by the control section 158, for example.

The communication section 156 is a communication device provided in the medical observation apparatus 100, and fulfills a role of communicating in a wireless or wired manner with an external apparatus such as the display apparatus 200. The communication section 156 includes the communication device (not illustrated) described above, for example. Communication in the communication section 156 is controlled by the control section 158, for example.

The control section 158 includes the processor (not illustrated) described above, for example, and fulfills a role of controlling the medical observation apparatus 100 overall. In addition, the control section 158 fulfills a role of leading the execution of the processes related to the control method described later.

More specifically, the control section 158 includes an imaging control section 160, an arm control section 162, and a display control section 164, for example.

The imaging control section 160 controls the imaging device 106 included in the imaging section 154. Examples of the control of the imaging device 106 include control of one or multiple functions typically provided in an electronic imaging microscope section, including control of at least a zoom function (one or both of an optical zoom function and an electronic zoom function), such as control of an AF function.

Additionally, the imaging control section 160 performs a cropping range control (described later) in the processes related to the control method according to the present embodiment.

The arm control section 162 controls the driving of the arm 104 included in the arm section 152. One example of control of the driving of the arm 104 includes, for example, "applying a control signal that controls driving to the actuators (not illustrated) corresponding to each of the joint sections 110*a*, 110*b*, 110*c*, 110*d*, and 110*e*", and the like.

Additionally, for example, the arm control section 162 performs a movement mechanism control (described later) in the processes related to the control method according to the present embodiment. Note that as the processes related to the control method according to the present embodiment, in the case in which only the cropping range control (described later) is performed, the medical observation apparatus 100 may also be a configuration in which the arm control section 162 does not perform the movement mechanism control (described later).

For example, the display control section 164 controls the display on the display apparatus 200 by conveying the display control signal and the image signal to the communication device (not illustrated) included in the communication section 156, and causing the display control signal and the image signal to be transmitted to the display apparatus 200. Note that the control of communication in the communication section 156 may also be performed by a communication control section (not illustrated) included in the control section 158.

For example, by including the imaging control section 160 and the arm control section 162, the control section 158 fulfills a role of leading the execution of the processes related to the control method according to the present embodiment. Also, for example, by including the imaging control section 160, the arm control section 162, and the display control section 164, the control section 158 fulfills a role of controlling the medical observation apparatus 100 overall.

Note that the configuration of the control section 158 is not limited to the example illustrated in FIG. 2.

For example, the control section 158 additionally may include a notification processing section that performs a notification process (described later) related to the control method according to the embodiment. In other words, for example, the control section 158 can include a configuration corresponding to the processes related to the control method according to the present embodiment performed in the medical observation apparatus 100.

Also, for example, the control section 158 can include an arbitrary configuration corresponding to how the functions included in the medical observation apparatus 100 are divided up, such as a configuration corresponding to how the processes related to the control method according to the present embodiment are divided up.

The medical observation apparatus 100 performs processes related to the control method according to the present embodiment described later with the configuration illustrated in FIG. 2, for example.

Note that the configuration of the medical observation apparatus according to the present embodiment is not limited to the configuration illustrated in FIG. 2.

For example, in the medical observation apparatus according to the present embodiment, one or more of the imaging control section 160, the arm control section 162, and the display control section 164 illustrated in FIG. 2 can be provided separately from the control section 158 (for example, realized by a different processing circuit).

Additionally, in the medical observation apparatus according to the present embodiment, the configuration for realizing processes related to the control method according to the present embodiment is not limited to the configuration illustrated in FIG. 2. For example, the medical observation apparatus according to the present embodiment can take a configuration corresponding to the processes related to the control method according to the present embodiment performed in the medical observation apparatus according to the present embodiment, or a configuration corresponding to how the processes related to the control method according to the present embodiment are divided up.

Also, for example, in the case of communicating with an external apparatus via an external communication device having a function and configuration similar to the communication section 156, the medical observation apparatus according to the present embodiment may also not be provided with the communication section 156.

Also, in the case in which the medical observation system according to the present embodiment includes the control apparatus (not illustrated), and the medical observation apparatus according to the present embodiment is controlled by the control apparatus (not illustrated), the medical observation apparatus according to the present embodiment may also not be provided with the control section 158.

Herein, the control apparatus (not illustrated) is, for example, provided with a control section having a function and configuration similar to the control section 158, and thereby performs processes related to the control method according to the present embodiment described later, and in addition, controls the operation in each structural element such as the arm section 152 and the imaging section 154 provided in the medical observation apparatus according to the present embodiment. The control apparatus (not illustrated) communicates with the medical observation apparatus according to the present embodiment via a provided communication device or a connected external communication device, and thereby controls the operation in each structural element provided in the medical observation apparatus according to the present embodiment.

[2] Processes Related to Control Method According to Present Embodiment

Next, processes related to the control method according to the present embodiment will be described. The following gives an example of a case in which the processes related to the control method according to the present embodiment are performed by the medical observation apparatus 100 (more specifically, the control section 158 included in the medical observation apparatus 100, for example). Note that, as described above, in the medical observation system according to the present embodiment, the processes related to the control method according to the present embodiment may also be performed by the control apparatus (not illustrated).

For example, in the case in which the imaging device 106 is supported by the arm 104 as illustrated in FIG. 1, one or both of the position and the attitude of the imaging device 106 may be moved freely. For this reason, in the case in which the imaging device 106 is supported by the arm 104, the user of the medical observation apparatus 100 is able to move the imaging field of view of the imaging device 106 as desired.

However, as described above, in the case in which the user of the medical observation apparatus 100 manually moves the imaging field of view, fine adjustment of the imaging field of view is difficult. Also, in the case in which the user of the medical observation apparatus 100 moves the imaging field of view by causing the movement mechanism to operate, a wait time until the movement of the imaging field of view is started occurs, which carries a risk of lowered user convenience. Herein, examples of the user of the medical observation apparatus 100 according to the present embodiment include medical personnel such as a surgeon or a surgeon's assistant.

Accordingly, the medical observation apparatus 100 controls the movement of the imaging field of view in the imaging device 106 on the basis of a predetermined operation related to the movement of the imaging field of view. Hereinafter, the movement of the imaging field of view in the imaging device 106 will be simply designated the "movement of the imaging field of view" in some cases.

Herein, examples of the predetermined operation related to the movement of the imaging field of view according to the present embodiment include an operation with respect to an operating device external to the medical observation apparatus 100, such as a footswitch or a remote controller, and an operation with respect to an operating device such as a switch provided on the medical observation apparatus 100. Hereinafter, the predetermined operation related to the movement of the imaging field of view will be simply designated the "predetermined operation" in some cases.

More specifically, for example, the medical observation apparatus 100 controls the movement of the imaging field of view by performing the cropping range control illustrated in (1) below, or by performing the cropping range control and the movement mechanism control illustrated in (2) below.

(1) Cropping Range Control

The medical observation apparatus 100 controls the movement of the imaging field of view by performing the cropping range control that crops the imaging range of the imaging device 106 on the basis of the predetermined operation.

Herein, the imaging range of the imaging device 106 according to the present embodiment refers to the imaging range of the image sensor included in the imaging device 106. In other words, the imaging range of the imaging device 106 corresponds to the imaging range that can be physically imaged by the imaging device 106.

Meanwhile, the cropping range according to the present embodiment refers to a range cropped from the imaging range of the imaging device 106. Examples of the cropping range include a range that is smaller than the imaging range of the imaging device 106. In other words, the number of imaging elements of the image sensor corresponding to the cropping range is less than the number of imaging elements of the image sensor corresponding to the imaging range of the imaging device 106.

By setting the cropping range, in the medical observation apparatus 100, a taken image illustrating the cropping range is obtained. Also, the shape of the cropping range is set in accordance with the desired shape of the taken image, such as rectangular, circular, or elliptical, for example.

Note that the region excluding the cropping range in the imaging range may also be utilized for various purposes, such as shake correction and adjustment of the imaging device 106, for example.

Figure 3:
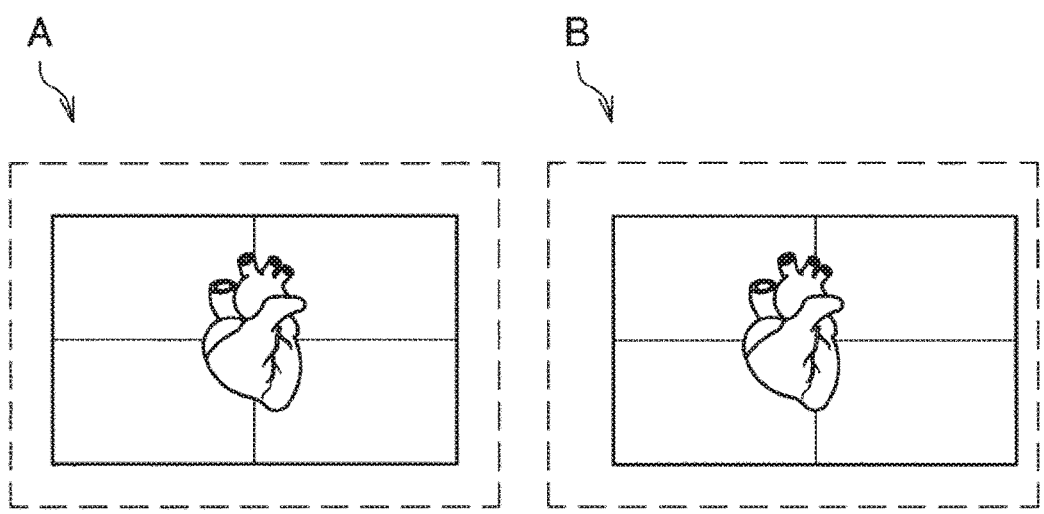
FIG. 3 is an explanatory diagram for explaining an example of a cropping range control related to a control method according to the present embodiment.

FIG. 3 is an explanatory diagram for explaining an example of the cropping range control according to the control method according to the present embodiment. A of FIG. 3 illustrates an imaging state of the imaging device 106 before movement of the imaging field of view by the cropping range control, while B of FIG. 3 illustrates an imaging state of the imaging device 106 after movement of the imaging field of view by the cropping range control. In FIG. 3, the observation target to be imaged by the imaging device 106, namely a patient's heart, is illustrated in a simplified manner.

For example, as illustrated in A of FIG. 3 and B of FIG. 3, by changing the cropping range, the position of the observation target in the cropping range changes. In the example illustrated in FIG. 3, by changing the cropping range to move in the right direction in FIG. 3, the position of the observation target in the cropping range moves in the left direction in FIG. 3. In other words, by causing the cropping range to change, it is possible to cause the imaging field of view to move.

Thus, by causing the cropping range to change in correspondence with the predetermined operation, the medical observation apparatus 100 can cause the imaging field of view to move according to the cropping range control.

For example, if a signal corresponding to the predetermined operation is acquired from an operating device such as a footswitch, the medical observation apparatus 100 changes the cropping range in the direction indicated by the signal.

In addition, while the above signal corresponding to the predetermined operation is being detected, the medical observation apparatus 100 controls the movement of the imaging field of view by performing the cropping range control so that, for example, the movement velocity of the imaging field of view is constant. By causing the imaging field of view to move so that the movement velocity of the imaging field of view is constant, a variety of advantages are obtained. For example, fine adjustment of the imaging field of view becomes easy, and visibility can be ensured for the person watching the taken image displayed on the display screen of the display apparatus 200.

Note that the cropping range control in the medical observation apparatus 100 is not limited to control so that the movement velocity of the imaging field of view is constant. For example, it is also possible for the medical observation apparatus 100 to cause the imaging field of view to move according to the cropping range control so that the movement velocity of the imaging field of view accelerates until a set upper limit is reached.

Herein, in the case in which the imaging field of view moves by the cropping range control, the wait time that could lead to lowered user convenience does not occur like in the case of causing the imaging field of view to move by the operation of the movement mechanism described above.

Consequently, by performing the cropping range control, the medical observation apparatus 100 can make an improvement in convenience.

(2) Cropping Range Control and Movement Mechanism Control

The medical observation apparatus 100 controls the movement of the imaging field of view by additionally performing the movement mechanism control on the basis of the predetermined operation, in addition to the cropping range control illustrated in (1) above.

As described above, by causing the cropping range to change in correspondence with the predetermined operation, the medical observation apparatus 100 causes the imaging field of view to move according to the cropping range control. In addition, by causing the movement mechanism to operate in correspondence with the predetermined operation, the medical observation apparatus 100 causes the imaging field of view to move according to the movement mechanism control.

For example, the medical observation apparatus 100 controls the movement of the imaging field of view by performing the cropping range control and the movement mechanism controls so that, for example, the movement velocity of the imaging field of view is constant.

Herein, the movement velocity of the imaging field of view in the case of performing the cropping range control and the movement mechanism control is expressed by Formula 1 below, for example.

Movement velocity of imaging field of view=(movement velocity of imaging field of view due to cropping range control)+(movement velocity of imaging field of view due to movement mechanism) (Formula 1)

Examples of the movement direction of the imaging field of view in the "movement velocity of imaging field of view due to cropping range control" indicated in Formula 1 above include the direction corresponding to the predetermined operation (for example, the direction indicated by the signal corresponding to the predetermined operation described above), or the opposite direction (the direction differing by 180[°]) of the direction corresponding to the predetermined operation. Also, examples of the movement direction of the "movement velocity of imaging field of view due to movement mechanism control" indicated in Formula 1 above include the direction corresponding to the predetermined operation, or the opposite direction of the direction corresponding to the predetermined operation. In other words, the relationship between movement direction of the imaging field of view in the "movement velocity of imaging field of view due to cropping range control" indicated in Formula 1 above and the movement direction of the "movement velocity of imaging field of view due to movement mechanism control" indicated in Formula 1 may be the same direction, or different directions.

As described above, by causing the imaging field of view to move so that the movement velocity of the imaging field of view is constant, a variety of advantages are obtained. For example, fine adjustment of the imaging field of view becomes easy, and visibility can be ensured for the person watching the taken image displayed on the display screen of the display apparatus 200. Note that the cropping range control and the movement mechanism control in the medical observation apparatus 100 obviously are not limited to control so that the movement velocity of the imaging field of view is constant.

In the case in which the predetermined operation is detected, the medical observation apparatus 100 starts the cropping range control and the movement mechanism control.

Figure 4:
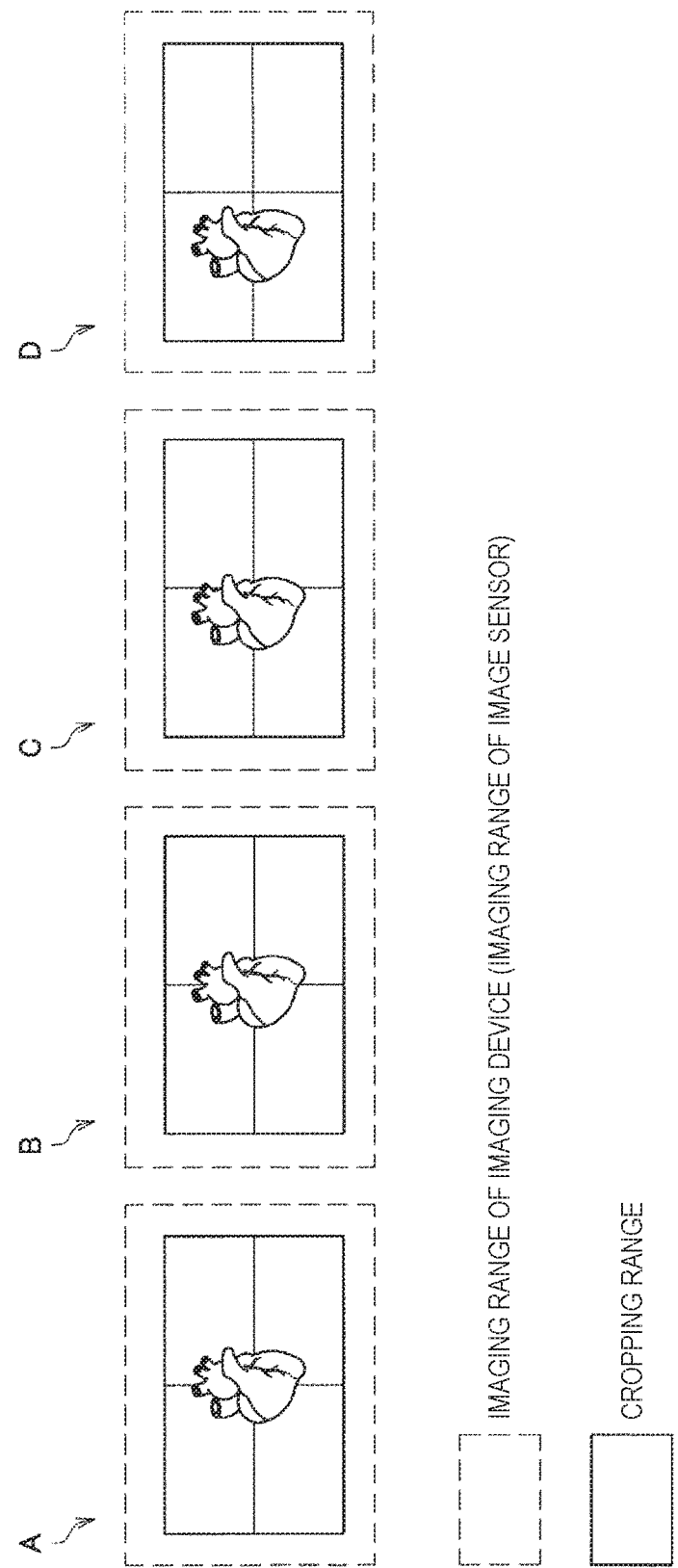
FIG. 4 is an explanatory diagram illustrating an example of movement of the imaging field of view by only operation of the movement mechanism.

FIG. 4 is an explanatory diagram illustrating an example of movement of the imaging field of view by only the operation of the movement mechanism. A of FIG. 4, B of FIG. 4, C of FIG. 4, and D of FIG. 4 chronologically illustrate the movement of the imaging field of view (movement in the right direction in FIG. 4) by only the operation of the movement mechanism, in the order of A of FIG. 4, B of FIG. 4, C of FIG. 4, and D of FIG. 4.

A of FIG. 4 illustrates an example of the imaging state of the imaging device before the movement of the imaging field of view starts.

B of FIG. 4 illustrates an example of the imaging state of the imaging device at a first point in time after the movement of the imaging field of view starts, and illustrates an example of the imaging state of the imaging device at a point in time when backlash filling in the movement mechanism has started. In the case in which the imaging field of view moves by only the operation of the movement mechanism, after the movement of the imaging field of view starts, backlash filling in the movement mechanism is started. As illustrated in B of FIG. 4, in the state in which the backlash filling has not completed, the imaging field of view does not move.

C of FIG. 4 illustrates an example of the imaging state of the imaging device at a second point in time (a point in time after the first point in time) after the movement of the imaging field of view starts, and illustrates an example of the imaging state of the imaging device at a point in time after the backlash filling in the movement mechanism has completed. As illustrated in C of FIG. 4, in the case in which the imaging field of view moves by only the operation of the movement mechanism, after the backlash filling is completed, the movement of the movement mechanism is started.

D of FIG. 4 illustrates an example of the imaging state of the imaging device at a third point in time (a point in time after the second point in time) after the movement of the imaging field of view starts, and illustrates an example of the imaging state of the imaging device in the case in which the movement of the imaging field of view by only the operation of the movement mechanism is being performed. As illustrated in D of FIG. 4, in the case in which the imaging field of view moves by only the operation of the movement mechanism, when the movement of the imaging field of view is started, the field of view continues to move.

For example, as illustrated in FIG. 4, in the case of causing the imaging field of view to move by only the operation of the movement mechanism, a wait time occurs until the movement of the imaging field of view by the movement mechanism starts. Thus, as described above, in the case of causing the imaging field of view to move by only the operation of the movement mechanism, there is a risk of lowered user convenience.

On the other hand, since the medical observation apparatus 100 starts the movement mechanism control together with the cropping range control, the movement of the imaging field of view is performed by the cropping range control even during the above wait time. In other words, in the case in which the cropping range control and the movement mechanism control are performed, the wait time associated with the movement of the imaging field of view by the movement mechanism is dispelled by the movement of the imaging field of view by the cropping range control.

Figure 5:
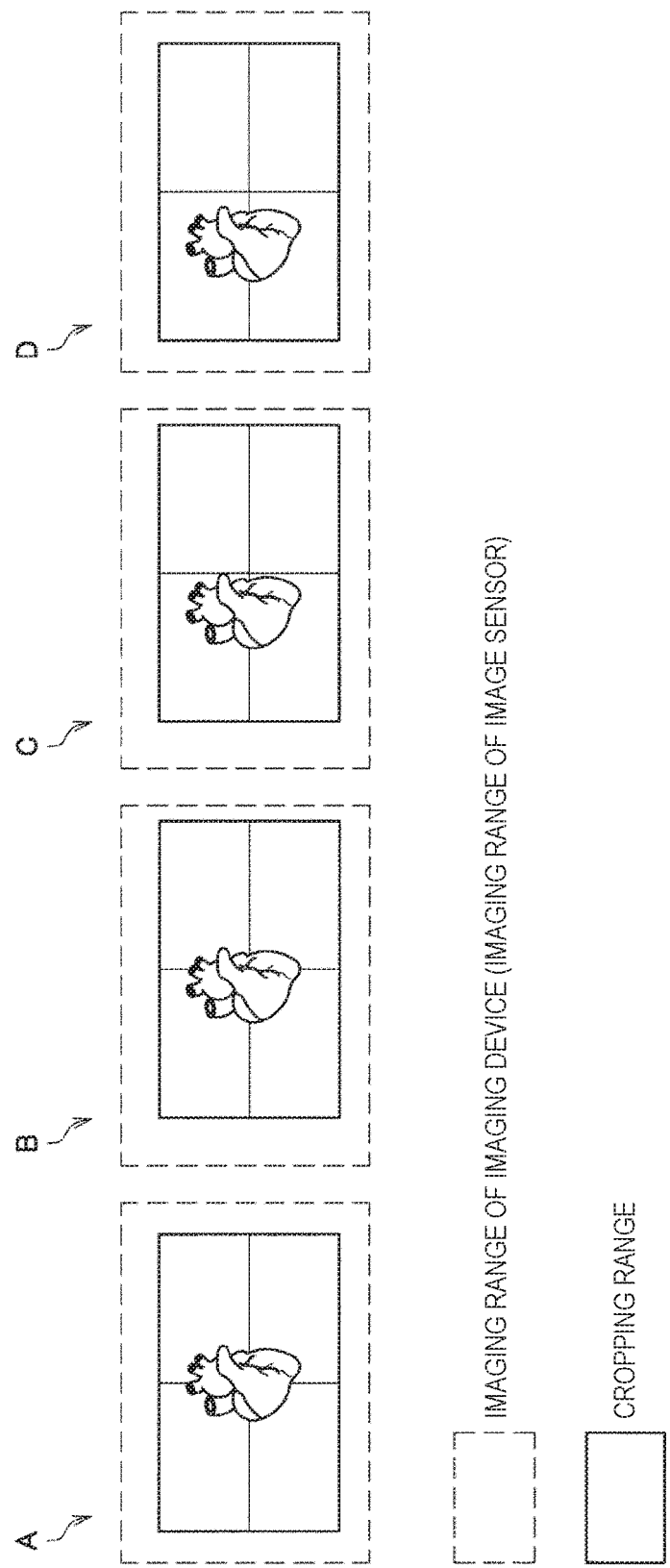
FIG. 5 is an explanatory diagram for explaining an example of the cropping range control and a movement mechanism control related to a control method according to the present embodiment.

FIG. 5 is an explanatory diagram for explaining an example of the cropping range control and the movement mechanism control related to the control method according to the present embodiment. A of FIG. 5, B of FIG. 5, C of FIG. 5, and D of FIG. 5 chronologically illustrate the movement of the imaging field of view (movement in the right direction in FIG. 5) by the cropping range control and the movement mechanism control, in the order of A of FIG. 5, B of FIG. 5, C of FIG. 5, and D of FIG. 5.

A of FIG. 5 illustrates an example of the imaging state of the imaging device before the movement of the imaging field of view starts.

B of FIG. 5 illustrates an example of the imaging state of the imaging device at a first point in time after the movement of the imaging field of view starts, and similarly to B of FIG. 4, illustrates an example of the imaging state of the imaging device at a point in time when backlash filling in the movement mechanism has started. In the case in which the imaging field of view moves by the cropping range control and the movement mechanism control, even in a state in which backlash filling in the movement mechanism has not completed, the movement of the imaging field of view is started by the cropping range control.

C of FIG. 5 illustrates an example of the imaging state of the imaging device at a second point in time (a point in time after the first point in time) after the movement of the imaging field of view starts, and similarly to C of FIG. 4, illustrates an example of the imaging state of the imaging device at a point in time after the backlash filling in the movement mechanism has completed. In the case in which the imaging field of view moves by the cropping range control and the movement mechanism control, after the backlash filling is completed, the movement of the imaging field of view by the movement mechanism is started.

In addition, after the movement of the imaging field of view by the movement mechanism starts, the medical observation apparatus 100 starts returning the cropping range to the state illustrated in A of FIG. 5. In other words, after the movement of the imaging field of view by the movement mechanism starts, the medical observation apparatus 100 performs the cropping range control to return the cropping range to the state before the cropping range control is performed.

Herein, the timing at which the medical observation apparatus 100 performs the cropping range control to return the cropping range to the state before the cropping range control is performed may be, as described later, for example, after it has become possible to perform the movement of the imaging field of view at a target field of view movement velocity with only the operation of the movement mechanism. Note that the timing at which to perform the above cropping range control obviously is not limited to the example illustrated above.

D of FIG. 5 illustrates an example of the imaging state of the imaging device at a third point in time (a point in time after the second point in time) after the movement of the imaging field of view starts, and illustrates an example of the imaging state of the imaging device in the case in which the movement of the imaging field of view is being performed. In the case in which the imaging field of view moves by the cropping range control and the movement mechanism control, when the cropping range returns to the state before the cropping range control is performed, the field of view continues to move by the movement mechanism.

For example, as illustrated in FIG. 5, by having the medical observation apparatus 100 perform the cropping range control and the movement mechanism control, the wait time associated with the movement of the imaging field of view by the movement mechanism is dispelled, and the user does not experience the wait time. Consequently, by performing the cropping range control and the movement mechanism control, the medical observation apparatus 100 can make an improvement in convenience.

Hereinafter, the movement of the imaging field of view when the cropping range control and the movement mechanism control are performed will be described by giving an example of a case in which the medical observation apparatus 100 controls the movement of the imaging field of view so that the movement velocity of the imaging field of view is constant.

In the following, the movement velocity of the imaging field of view that the medical observation apparatus 100 attempts to keep constant will be designated the "target field of view movement velocity". The value of the target field of view movement velocity according to the present embodiment may be, for example, a preset fixed value, or a variable value that is changeable on the basis of a user operation or the like. Also, the value of the target field of view movement velocity according to the present embodiment may be, for example, a value set with respect to the medical observation apparatus 100, or a per-user value associated with an ID of a user who uses the medical observation apparatus 100. For example, the medical observation apparatus 100 specifies the value of the target field of view movement velocity by reading out information indicating the target field of view movement velocity from a recording medium (not illustrated).

(I) First Example of Cropping Range Control and Movement Mechanism Control: Example of Cropping Range Control and Movement Mechanism Control in Case in which Predetermined Operation Continues to be Performed First an example of the cropping range control and the movement mechanism control in a case in which the predetermined operation continues to be performed will be described.

Figure 6:
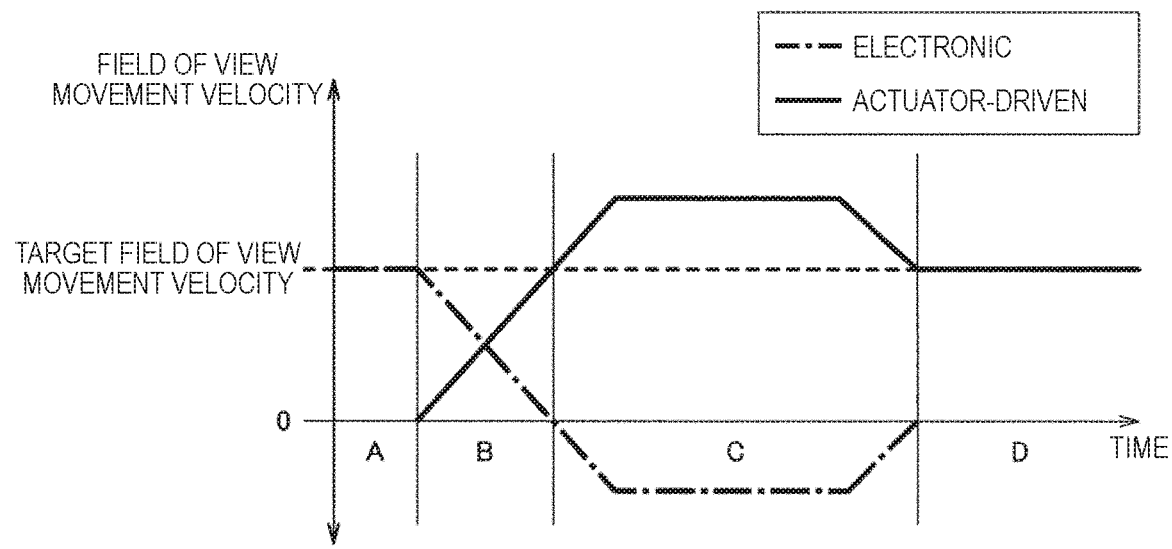
FIG. 6 is an explanatory diagram for explaining a first example of movement of the imaging field of view by the cropping range control and the movement mechanism control related to a control method according to the present embodiment.

FIG. 6 is an explanatory diagram for explaining a first example of the movement of the imaging field of view by the cropping range control and the movement mechanism control related to the control method according to the present embodiment, and illustrates an example of the cropping range control and the movement mechanism control in the case in which the predetermined operation continues to be performed.

In FIG. 6, the movement of the imaging field of view by the cropping range control is labeled "electronic", while the movement of the imaging field of view by the movement mechanism control is labeled "actuator-driven" (hereinafter, the same applies to FIGS. 7 to 9 described later). Also, the case in which the field of view movement velocity takes a positive value in FIG. 6 indicates that the imaging field of view is moving in the direction corresponding to the predetermined operation, while the case in which the field of view movement velocity takes a negative value in FIG. 6 indicates that the imaging field of view is moving in the opposite direction of the direction corresponding to the predetermined operation (hereinafter, the same applies to FIGS. 7 to 9 described later).

(I-1) Period A of FIG. 6

In the case in which the predetermined operation is detected, the medical observation apparatus 100 starts the cropping range control and the movement mechanism control. For example, in the case in which the signal corresponding to the predetermined operation is detected, the medical observation apparatus 100 determines that the predetermined operation is detected.

As described above, even if the movement mechanism control is started, a wait time occurs until the movement of the imaging field of view by the movement mechanism starts. For this reason, as illustrated in the period A of FIG. 6, until the above wait time elapses, the imaging field of view moves by only the cropping range control.

(I-2) Period B of FIG. 6

When the backlash filling in the movement mechanism is completed, the movement of the imaging field of view by the movement mechanism is started, and the imaging field of view moves by changes in the cropping range and the operation of the movement mechanism.

At this time, the medical observation apparatus 100 adjusts the movement velocity of the imaging field of view by the cropping range control so that the movement velocity of the imaging field of view becomes the target field of view movement velocity. Specifically, the medical observation apparatus 100 adjusts the movement velocity of the imaging field of view by the cropping range control on the basis of Formula 1 above. In other words, as illustrated in the period B of FIG. 6, the medical observation apparatus 100 lowers the movement velocity of the imaging field of view by the cropping range control by the amount that the movement velocity of the imaging field of view by the movement mechanism control rises.

(I-3) Period C of FIG. 6

In the case in which the movement velocity of the imaging field of view by the movement mechanism control reaches the target field of view movement velocity, the medical observation apparatus 100 performs the cropping range control to return the cropping range to the state before the cropping range control is performed, as illustrated with reference to FIG. 5, for example. Herein, the case in which the movement velocity of the imaging field of view by the movement mechanism control reaches the target field of view movement velocity corresponds to the case in which it has become possible to perform the movement of the imaging field of view at the target field of view movement velocity with only the operation of the movement mechanism.

At this time, the medical observation apparatus 100 adjusts the movement velocity of the imaging field of view by the movement mechanism control so that the movement velocity of the imaging field of view becomes the target field of view movement velocity. Specifically, the medical observation apparatus 100 adjusts the movement velocity of the imaging field of view by the movement mechanism control on the basis of Formula 1 above. As illustrated in the period C of FIG. 6, the medical observation apparatus 100 raises the movement velocity of the imaging field of view by the movement mechanism control to cancel out the movement of the imaging field of view by the cropping range control that moves in the opposite direction of the direction corresponding to the predetermined operation.

In other words, in the case in which the cropping range control that returns the cropping range is performed, the medical observation apparatus 100 performs the movement mechanism control to raise the movement velocity of the imaging field of view by the movement mechanism in correspondence with the cropping range control that returns the cropping range.

(I-4) Period D of FIG. 6

When the cropping range control that returns the cropping range is completed, the medical observation apparatus 100 causes the imaging field of view to move by performing the movement mechanism control on the basis of the predetermined operation. Additionally, when the cropping range control that returns the cropping range is completed, the medical observation apparatus 100 stops the execution of the cropping range control.

Thus, as illustrated in the period D of FIG. 6, when the cropping range control that returns the cropping range is completed, the imaging field of view moves by only the operation of the movement mechanism.

In the case in which the predetermined operation continues to be performed, as illustrated in FIG. 6, for example, by performing each of the movement of the imaging field of view by the cropping range control and the movement of the imaging field of view by the movement mechanism control, the imaging field of view moves so that the movement velocity is constant.

Note that an example of the cropping range control and the movement mechanism control in the case in which the predetermined operation continues to be performed is not limited to the example illustrated in FIG. 6.

Figure 7:
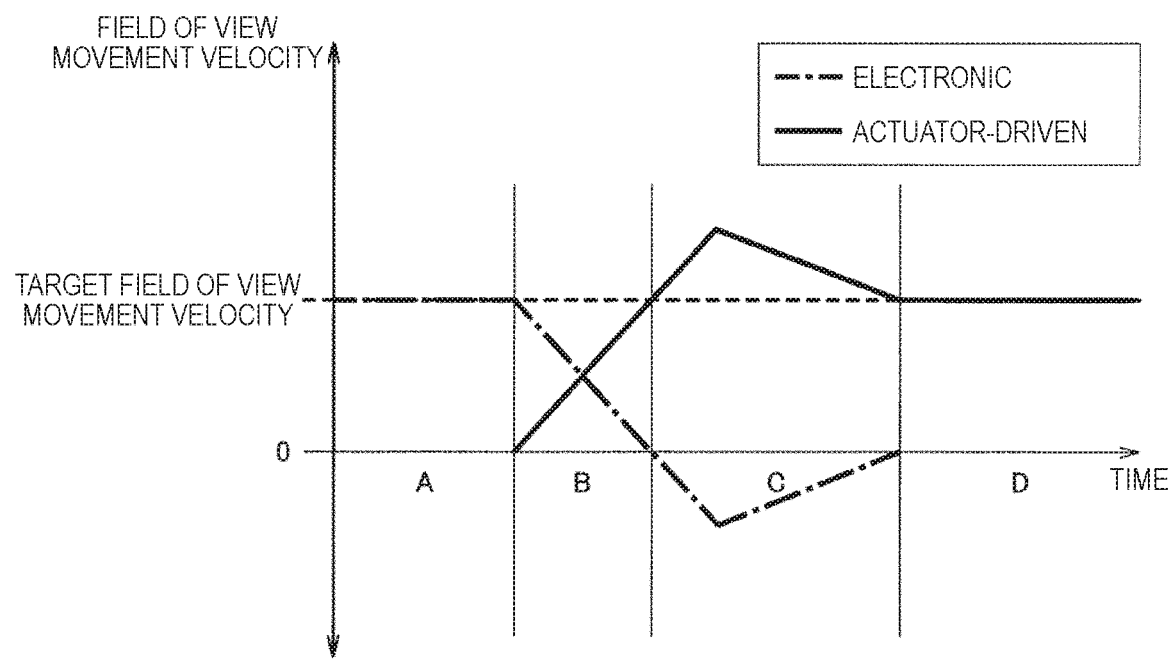
FIG. 7 is an explanatory diagram for explaining a second example of movement of the imaging field of view by the cropping range control and the movement mechanism control related to a control method according to the present embodiment.

FIG. 7 is an explanatory diagram for explaining a second example of the movement of the imaging field of view by the cropping range control and the movement mechanism control related to the control method according to the present embodiment, and illustrates another example of the cropping range control and the movement mechanism control in the case in which the predetermined operation continues to be performed.

The period A, period B, period C, and period D illustrated in FIG. 7 correspond to the period A, period B, period C, and period D illustrated in FIG. 6, respectively. Also, in each of the periods A, B, C, and D illustrated in FIG. 7, the medical observation apparatus 100 performs the cropping range control and the movement mechanism control similarly to each of the periods A, B, C, and D illustrated in FIG. 6.

As illustrated in the period A illustrated in FIG. 7 and the period A illustrated in FIG. 6, the length of the period in which the imaging field of view moves by only the cropping range control may vary depending on factors such as the hardware performance of the medical observation apparatus 100, and the design of the medical observation apparatus 100, for example. Also, as illustrated in the period C illustrated in FIG. 7 and the period C illustrated in FIG. 6, the way in which the cropping range control that returns the cropping range is performed and the way in which the movement mechanism control corresponding to the cropping range control that returns the cropping range is performed may vary depending on factors such as the hardware performance of the medical observation apparatus 100, and the design of the medical observation apparatus 100, for example.

(II) Second Example of Cropping Range Control and Movement Mechanism Control: Example of Cropping Range Control and Movement Mechanism Control in Case in which Stopping of Predetermined Operation is Detected Next an example of the cropping range control and the movement mechanism control will be described for a case in which the stopping of the predetermined operation is detected after the predetermined operation is detected.

Figure 8:
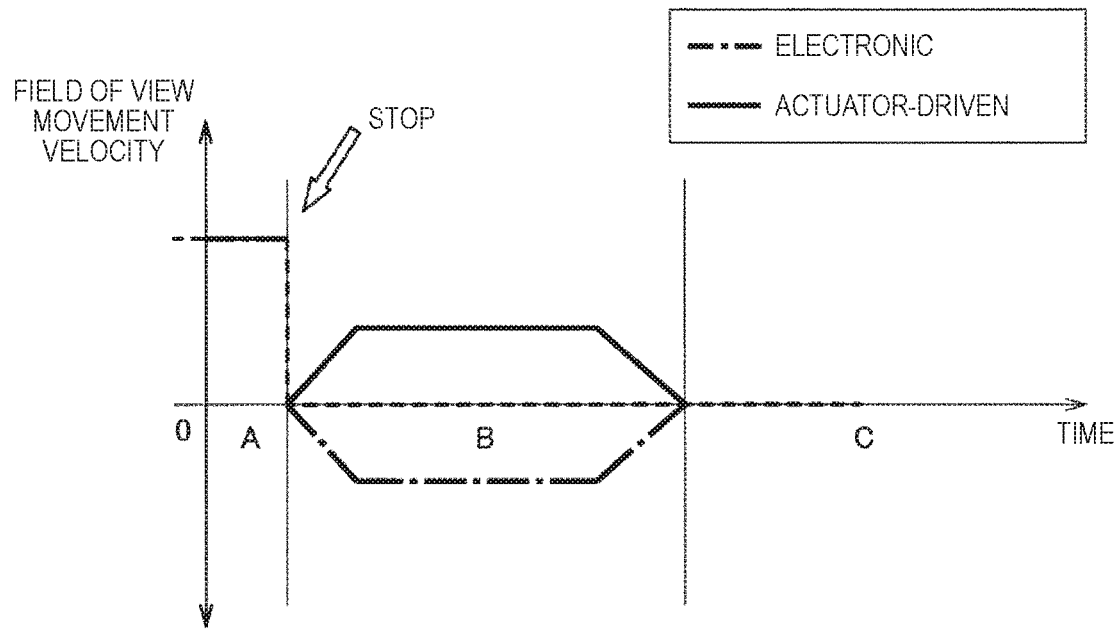
FIG. 8 is an explanatory diagram for explaining a third example of movement of the imaging field of view by the cropping range control and the movement mechanism control related to a control method according to the present embodiment.

FIG. 8 is an explanatory diagram for explaining a third example of the movement of the imaging field of view by the cropping range control and the movement mechanism control related to the control method according to the present embodiment. FIG. 8 illustrates an example of the cropping range control and the movement mechanism control for a "case in which the stopping of the predetermined operation is detected after the cropping range control and the movement mechanism control are started, but before the movement of the imaging field of view by the movement mechanism is started".

For example, in the case in which, after determining that the predetermined operation is detected, the signal corresponding to the predetermined operation is no longer detected, the medical observation apparatus 100 determines that the stopping of the predetermined operation is detected. Note that the method of detecting the stopping of the predetermined operation obviously is not limited to the example illustrated above.

Additionally, in the case of determining that the stopping of the predetermined operation is detected, the medical observation apparatus 100 may also re-set the target field of view movement velocity to a movement velocity of the imaging field of view corresponding to the stopping of the predetermined operation. An example of the movement velocity of the imaging field of view corresponding to the stopping of the predetermined operation includes 0 (zero). By re-setting the target field of view movement velocity to the movement velocity of the imaging field of view corresponding to the stopping of the predetermined operation, in the medical observation apparatus 100, as illustrated in the period B of FIG. 8 described later, for example, the cropping range control and the movement mechanism control are performed so that the movement velocity of the imaging field of view becomes the movement velocity of the imaging field of view corresponding to the stopping of the predetermined operation.

(II-1) Period A of FIG. 8

Similarly to the period A of FIG. 6, in the case in which the predetermined operation is detected, the medical observation apparatus 100 starts the cropping range control and the movement mechanism control. In the period A of FIG. 8, similarly to the period A of FIG. 6, the imaging field of view moves by only the cropping range control. In other words, the period A of FIG. 8 corresponds to a "period after the cropping range control and the movement mechanism control are started, but before the movement of the imaging field of view by the movement mechanism is started".

Herein, in the case in which the stopping of the predetermined operation is detected in the period A of FIG. 8, or in other words, in the case in which the stopping of the predetermined operation is detected after the cropping range control and the movement mechanism control are started, but before the movement of the imaging field of view by the movement mechanism is started, the medical observation apparatus 100 stops the execution of each of the cropping range control and the movement mechanism control.

Note that the process in the case in which the stopping of the predetermined operation is detected after the cropping range control and the movement mechanism control are started, but before the movement of the imaging field of view by the movement mechanism is started, is not limited to the example illustrated above.

For example, in the case of stopping the execution of each of the cropping range control and the movement mechanism control, the medical observation apparatus 100 may selectively perform the cropping range control that returns the cropping range described with reference to the period C of FIG. 6, for example, on the basis of the movement amount of the imaging field of view by the cropping range control when the stopping of the predetermined operation was detected.

More specifically, for example, the medical observation apparatus 100 computes the movement amount of the imaging field of view by the cropping range control above by multiplying the time from the detection of the predetermined operation until the detection of the stopping of the predetermined operation by the target field of view movement velocity.

In addition, the medical observation apparatus 100 compares the computed movement amount of the imaging field of view by the cropping range control to a set threshold value. Herein, the threshold value may be a preset fixed value, or a variable value that is changeable on the basis of a user operation or the like.

Subsequently, in the case in which the computed movement amount of the imaging field of view by the cropping range control is equal to or greater than the set threshold value (or in the case in which the movement amount is greater than the threshold value), the medical observation apparatus 100 performs the control illustrated with reference to the period B of FIG. 8. Also, in the case in which the computed movement amount of the imaging field of view by the cropping range control is less than the set threshold value (or in the case in which the movement amount is less than or equal to the threshold value), the medical observation apparatus 100 does not perform the control illustrated with reference to the period B of FIG. 8.

(II-2) Period B of FIG. 8

For example, similarly to the period C of FIG. 6, the medical observation apparatus 100 performs the cropping range control to return the cropping range to the state before the cropping range control is performed, and in addition, performs the movement mechanism control so that the movement velocity of the imaging field of view becomes the movement velocity corresponding to the stopping of the predetermined operation.

Note that, as described above, the control illustrated in the period B of FIG. 8 may also be performed selectively on the basis of the movement amount of the imaging field of view by the cropping range control when the stopping of the predetermined operation was detected.

(II-3) Period C of FIG. 8

When the cropping range control to return the cropping range is performed in the period B of FIG. 8, and the cropping range control is completed, the medical observation apparatus 100 stops the execution of each of the cropping range control and the movement mechanism control, as illustrated in the period C of FIG. 8.

In the "case in which the stopping of the predetermined operation is detected after the cropping range control and the movement mechanism control are started, but before the movement of the imaging field of view by the movement mechanism is started", as illustrated in FIG. 8, for example, by performing each of the cropping range control and the movement mechanism control, the movement of the imaging field of view stops.

Note that the example of the control in the "case in which the stopping of the predetermined operation is detected after the cropping range control and the movement mechanism control are started, but before the movement of the imaging field of view by the movement mechanism is started" obviously is not limited to the example illustrated in FIG. 8.

(III) Third Example of Cropping Range Control and Movement Mechanism Control: Another Example of Cropping Range Control and Movement Mechanism Control in Case in which Stopping of Predetermined Operation is Detected Next another example of the cropping range control and the movement mechanism control will be described for the case in which the stopping of the predetermined operation is detected after the predetermined operation is detected.

Figure 9:
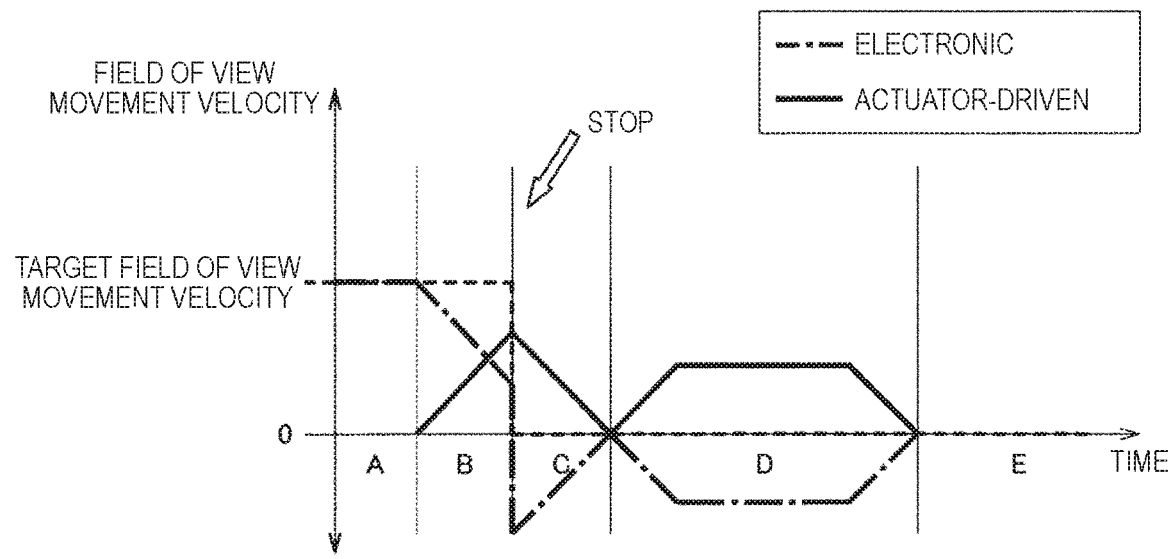
FIG. 9 is an explanatory diagram for explaining a fourth example of movement of the imaging field of view by the cropping range control and the movement mechanism control related to a control method according to the present embodiment.

FIG. 9 is an explanatory diagram for explaining a fourth example of the movement of the imaging field of view by the cropping range control and the movement mechanism control related to the control method according to the present embodiment. FIG. 9 illustrates an example of the cropping range control and the movement mechanism control for a "case in which the stopping of the predetermined operation is detected after the movement of the imaging field of view by the movement mechanism is started, but before the movement velocity of the imaging field of view by the movement mechanism becomes the set target field of view movement velocity".

(III-1) Period A of FIG. 9

Similarly to the period A of FIG. 6, in the case in which the predetermined operation is detected, the medical observation apparatus 100 starts the cropping range control and the movement mechanism control. In the period A of FIG. 9, similarly to the period A of FIG. 6, the imaging field of view moves by only the cropping range control.

(III-2) Period B of FIG. 9

When the backlash filling in the movement mechanism is completed, the movement of the imaging field of view by the movement mechanism is started, and similarly to the period B of FIG. 6, the imaging field of view moves by changes in the cropping range and the operation of the movement mechanism.

At this point, the case in which the stopping of the predetermined operation is detected in the period B of FIG. 9 is supposed. The case in which the stopping of the predetermined operation is detected in the period B of FIG. 9 corresponds to the "case in which the stopping of the predetermined operation is detected after the movement of the imaging field of view by the movement mechanism is started, but before the movement velocity of the imaging field of view by the movement mechanism becomes the set target field of view movement velocity".

In the case in which the stopping of the predetermined operation is detected in the period B of FIG. 9, the medical observation apparatus 100 re-sets the target field of view movement velocity to the movement velocity of the imaging field of view corresponding to the stopping of the predetermined operation. Subsequently, the medical observation apparatus 100 performs the control illustrated with reference to the period C of FIG. 9.

(III-3) Period C of FIG. 9

In the case in which the stopping of the predetermined operation is detected in the period B of FIG. 9, the medical observation apparatus 100 performs the cropping range control and the movement mechanism control so that the movement velocity of the imaging field of view becomes the movement velocity of the imaging field of view corresponding to the stopping of the predetermined operation.

Specifically, as illustrated in the period C of FIG. 9, the medical observation apparatus 100 performs the movement mechanism control so that the movement velocity of the imaging field of view by the movement mechanism falls, and in addition, performs the cropping range control so that the movement velocity of the imaging field of view becomes the movement velocity corresponding to the stopping of the predetermined operation. For example, on the basis of Formula 1 above, the medical observation apparatus 100 adjusts each of the movement velocity of the imaging field of view by the movement mechanism and the movement velocity of the imaging field of view by the cropping range control to become the movement velocity of the imaging field of view corresponding to the stopping of the predetermined operation.

(III-4) Period D of FIG. 9

In the case in which, by the control in the period C of FIG. 9, the movement velocity of the imaging field of view by the movement mechanism becomes the movement velocity corresponding to the stopping of the predetermined operation, for example, similarly to the period C of FIG. 6, the medical observation apparatus 100 performs the cropping range control to return the cropping range to the state before the cropping range control is performed, and in addition, performs the movement mechanism control so that the movement velocity of the imaging field of view becomes the movement velocity corresponding to the stopping of the predetermined operation.

Note that, similarly to the control illustrated in the period B of FIG. 8, the control illustrated in the period D of FIG. 9 may also be performed selectively on the basis of the movement amount of the imaging field of view by the cropping range control when the stopping of the predetermined operation was detected.

(III-5) Period E of FIG. 9

When the cropping range control to return the cropping range is performed in the period D of FIG. 9, and the cropping range control is completed, the medical observation apparatus 100 stops the execution of each of the cropping range control and the movement mechanism control, as illustrated in the period E of FIG. 9.

In the "case in which the stopping of the predetermined operation is detected after the movement of the imaging field of view by the movement mechanism is started, but before the movement velocity of the imaging field of view by the movement mechanism becomes the set target field of view movement velocity", as illustrated in FIG. 9, for example, by performing each of the cropping range control and the movement mechanism control, the movement of the imaging field of view stops.

Note that the example of the control in the "case in which the stopping of the predetermined operation is detected after the movement of the imaging field of view by the movement mechanism is started, but before the movement velocity of the imaging field of view by the movement mechanism becomes the set target field of view movement velocity" obviously is not limited to the example illustrated in FIG. 9.

(IV) Another Example of Cropping Range Control and Movement Mechanism Control

Note that an example in which the cropping range control and the movement mechanism control are performed is not limited to the first example illustrated in (I) above to the third example illustrated in (III) above.

For example, in the case in which the stopping of the predetermined operation is detected while the control of the period D of FIG. 6 in the first example illustrated in (I) above is being performed, the medical observation apparatus 100 stops the execution of the movement mechanism control. Additionally, at this time, the medical observation apparatus 100 may also perform a control similar to the controls illustrated in the period C and the period D of FIG. 9.

In addition, for example, in the case in which the movement amount of the imaging field of view based on the predetermined operation falls below a minimum movement amount that the imaging field of view can be made to move by the movement mechanism, the medical observation apparatus 100 causes the imaging field of view to move by only the cropping range control. For example, the movement amount of the imaging field of view based on the predetermined operation is computed according to the time from the detection of the predetermined operation until the detection of the stopping of the predetermined operation, and the movement velocity of the imaging field of view. In addition, the minimum movement amount that the imaging field of view can be made to move by the movement mechanism is determined by factors such as the hardware configuration of the movement mechanism, for example, and thus is set during the design phase or the manufacturing phase of the medical observation apparatus 100.

As processes related to the control method according to the present embodiment, for example, the medical observation apparatus 100 performs the processes illustrated in (1) above (processes related to the cropping range control), or the processes illustrated in (2) above (processes related to the cropping range control and the movement mechanism control).

Note that the processes related to the control method according to the present embodiment are not limited to the processes illustrated in (1) above and the processes illustrated in (2) above.

For example, the medical observation apparatus 100 may also issue to the user a notification regarding manual movement of the imaging field of view.

Examples of the notification regarding the manual movement of the imaging field of view according to the present embodiment include one or both of a notification for informing the user that "it is necessary to move the imaging field of view manually", and a notification for informing the user that "it is not necessary to move the imaging field of view manually".

For example, the medical observation apparatus 100 issues, by an arbitrary notification method, a notification regarding the manual movement of the imaging field of view, such as a "visual notification by causing text or an image to be displayed on a display screen, or by causing an indicator lamp to turn on", an "auditory notification by causing audio to be output from an audio output device such as a speaker", or a "notification combining these notifications".

Note that in the case in which the medical observation apparatus 100 includes the function of moving the imaging field of view by the movement mechanism control, by having the movement mechanism control be performed, the user is able to cause the imaging field of view to move arbitrarily. In other words, in the case in which the medical observation apparatus 100 includes the function of moving the imaging field of view by the movement mechanism control, the user can cause the imaging field of view to move arbitrarily, without manually moving the imaging field of view. Thus, in the case in which the medical observation apparatus 100 includes the function of moving the imaging field of view by the movement mechanism control, the medical observation apparatus 100 may also not issue to the user the notification regarding the manual movement of the imaging field of view.

On the other hand, in the case in which the medical observation apparatus 100 does not include the function of moving the imaging field of view by the movement mechanism control, the user may need to manually move the imaging field of view to cause the imaging field of view to move arbitrarily. Thus, in the case in which the medical observation apparatus 100 does not include the function of moving the imaging field of view by the movement mechanism control, the medical observation apparatus 100 issues to the user the notification regarding the manual movement of the imaging field of view.

In the case of issuing the notification regarding the manual movement of the imaging field of view, for example, the medical observation apparatus 100 specifies a positional relationship between a movable range of the imaging field of view by the cropping range control set inside the imaging range, and the cropping range. Subsequently, on the basis of the specified positional relationship between the movable range of the imaging field of view by the cropping range control and the cropping range, the medical observation apparatus 100 issues the notification regarding the manual movement of the imaging field of view. Hereinafter, the relationship between the movable range of the imaging field of view by the cropping range control and the cropping range will be designated the "range positional relationship" in some cases.

FIG. 10 is an explanatory diagram for describing an example of a notification-related process related the control method according to the present embodiment.

A of FIG. 10 illustrates the imaging range of the imaging device 106.

B of FIG. 10 illustrates the range in which the center position of the cropping range can be moved inside the imaging range, and corresponds to an example of the movable range of the imaging field of view by the cropping range control. In other words, B of FIG. 10 is the movement range of the center position of the cropping range in which the cropping range can be contained inside the imaging range illustrated by A of FIG. 10.

C of FIG. 10 is the range in which the cropping range control that returns the cropping range described above does not have to be performed in the case in which the movement of the imaging field of view by the cropping range control is performed. Note that, in the case in which the center position of the cropping range is inside the range illustrated by C of FIG. 10 as a result of performing the movement of the imaging field of view by the cropping range control, the medical observation apparatus 100 obviously may also perform the cropping range control that returns the cropping range described above.

Examples of the range illustrated by C of FIG. 10 include the range in which the imaging field of view is made to move by only the cropping range control, such as the range of falling below the minimum movement amount that the imaging field of view can be made to move by the movement mechanism described above.

For example, the medical observation apparatus 100 specifies the range positional relationship by specifying the positional relationship between the center position of the cropping range set by the cropping range control, and the range illustrated by B of FIG. 10. Examples of the center position of the cropping range include the position of the intersection point of the diagonals corresponding to the cropping range. Examples of the diagonals corresponding to the cropping range include the diagonals of a rectangular cropping range, the diagonals of a rectangular range containing a circular or elliptical cropping range, or the like.

For example, the medical observation apparatus 100 specifies the positional relationship between the center position of the cropping range and the range illustrated by B of FIG. 10 by computing the distance between "the coordinates of the intersection point of the diagonals corresponding to the cropping range" and "the coordinates of the position on the perimeter of the range illustrated by B of FIG. 10 corresponding to the movement direction of the imaging field of view". Coordinates inside the imaging range are expressed by two-dimensional coordinates taking an arbitrary point inside the imaging range as the origin, such as by taking the center position of the imaging range as the origin, for example. Also, examples of the distance between "the coordinates of the intersection point of the diagonals corresponding to the cropping range" and "the coordinates of the position on the perimeter of the range illustrated by B of FIG. 10 corresponding to the movement direction of the imaging field of view" include the Euclidean distance between "the coordinates of the intersection point of the diagonals corresponding to the cropping range" and "the coordinates of the position on the perimeter of the range illustrated by B of FIG. 10 corresponding to the movement direction of the imaging field of view".

Subsequently, the medical observation apparatus 100 compares the computed distance above and a set distance-related threshold value, and issues the notification regarding the manual movement of the imaging field of view according to the comparison result. The distance-related threshold value may be a preset fixed value, or a variable value that is changeable on the basis of a user operation or the like.

To give one example of the case of issuing the notification regarding the manual movement of the imaging field of view, for example, in the case in which the computed distance above is less than or equal to the distance-related threshold value (or in the case in which the distance above is less than the distance-related threshold value), the medical observation apparatus 100 issues the notification for informing the user that "it is necessary to move the imaging field of view manually" (one example of the notification regarding the manual movement of the imaging field of view). By issuing the notification for informing the user that "it is necessary to move the imaging field of view manually", the user is able to recognize that the medical observation apparatus 100 may need the imaging field of view to be moved manually.

Also, to give another example of the case of issuing the notification regarding the manual movement of the imaging field of view, for example, in the case in which the computed distance above is greater than the distance-related threshold value (or in the case in which the distance above is equal to or greater than the distance-related threshold value), the medical observation apparatus 100 issues the notification for informing the user that "it is not necessary to move the imaging field of view manually" (one example of the notification regarding the manual movement of the imaging field of view). By issuing the notification for informing the user that "it is not necessary to move the imaging field of view manually", the user is able to recognize that the medical observation apparatus 100 does not need the imaging field of view to be moved manually.

Note that the medical observation apparatus 100 may also issue only one of the above notification for informing the user that "it is necessary to move the imaging field of view manually" and the above notification for informing the user that "it is not necessary to move the imaging field of view manually".

For example, by issuing the notification regarding the manual movement of the imaging field of view on the basis of the range positional relationship as described above, the medical observation apparatus 100 can cause the user to recognize whether or not the medical observation apparatus 100 is in a state in which the imaging field of view may need to be moved manually.

Note that, as described above, in the case in which the medical observation apparatus 100 includes the function of moving the imaging field of view by the movement mechanism control, by having the movement mechanism control be performed, the user can cause the imaging field of view to move arbitrarily, without manually moving the imaging field of view. Thus, in the case in which the medical observation apparatus 100 includes the function of moving the imaging field of view by the movement mechanism control, the medical observation apparatus 100 may also not issue to the user the notification regarding the manual movement of the imaging field of view.

[3] Example of Effects Exhibited by Using Medical Observation Apparatus According to Present Embodiment (or Control Apparatus According to Present Embodiment By using the medical observation apparatus according to the present embodiment (or the control apparatus according to the present embodiment), for example, the effects indicated below are exhibited. Note that the effects exhibited by using the medical observation apparatus according to the present embodiment (or the control apparatus according to the present embodiment) obviously are not limited to the effects indicated below.

Since the movement of the imaging field of view by the cropping range control is performed as an initial move corresponding to the predetermined operation related to user movement of the imaging field of view, the wait time associated with the movement of the imaging field of view by the movement mechanism is dispelled. Thus, a delay-free and smooth start of the movement of the imaging field of view in response to the predetermined operation performed by a user such as a physician can be realized.

By the cropping range control and the movement mechanism control, the imaging field of view moves without remaining when the predetermined operation related to the user movement of the imaging field of view is performed, and thus the user is able to obtain a stress-free sense of operability.

By performing the cropping range control and the movement mechanism control so that the movement velocity of the imaging field of view is maintained at the target field of view movement velocity, a variety of advantages are obtained. For example, fine adjustment of the imaging field of view becomes easy, and visibility can be ensured for the person watching the taken image displayed on the display screen of the display apparatus 200 or the like.

By performing the cropping range control that returns the cropping range together with the movement mechanism control, the movement velocity of the imaging field of view can be maintained at the target field of view movement velocity, while at the same time, the cropping range can be returned to the state before the cropping range control is performed, such as by returning the cropping range to the center position of the imaging range.

(Program According to Present Embodiment)

By having a program (for example, a program capable of executing the processes related to the control method according to the present embodiment) for causing a computer system to function as the medical observation apparatus according to the present embodiment (or the control apparatus according to the present embodiment) be executed by a processor or the like in a computer system, an improvement in convenience can be made. Herein, a computer system according to the present embodiment includes a single computer, or multiple computers. A series of processes related to the control method according to the present embodiment is performed by the computer system according to the present embodiment.

Additionally, by having the program for causing a computer system to function as the medical observation apparatus according to the present embodiment (or the control apparatus according to the present embodiment) be executed by a processor or the like in the computer system, the effects exhibited by the processes related to the control method according to the present embodiment described above can be exhibited.

It should be understood by those skilled in the art that various modifications, combinations, sub-combinations and alterations may occur depending on design requirements and other factors insofar as they are within the scope of the appended claims or the equivalents thereof.

For example, although the foregoing indicates that a program (computer program) for causing a computer system to function as the medical observation apparatus according to the present embodiment (or the control apparatus according to the present embodiment) is provided, the present embodiment can additionally provide a recording medium storing the above program.

The configuration described above illustrates one example of the present embodiment, and rightfully belongs to the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1) A medical observation apparatus including:
a control section configured to control, on a basis of a predetermined operation related to a movement of an imaging field of view, the movement of the imaging field of view in an imaging device supported by an arm including a plurality of links joined to each other by joint sections, in which
the control section controls the movement of the imaging field of view by performing a cropping range control that crops an imaging range of the imaging device on the basis of the predetermined operation.

(2) The medical observation apparatus according to (1), in which
the control section causes the imaging field of view to move by the cropping range control by causing the cropping range inside the imaging range to change in correspondence with the predetermined operation.

(3) The medical observation apparatus according to (1) or (2), in which
the control section controls the movement of the imaging field of view by additionally performing a movement mechanism control that moves the arm to cause the imaging field of view to move, on the basis of the predetermined operation.

(4) The medical observation apparatus according to (3), in which
the control section causes the imaging field of view to move by the movement mechanism control by causing the movement mechanism to operate in correspondence with the predetermined operation.

(5) The medical observation apparatus according to (3) or (4), in which
in a case in which the predetermined operation is detected, the control section starts the cropping range control and the movement mechanism control.

(6) The medical observation apparatus according to (5), in which after the movement of the imaging field of view by the movement mechanism starts, the control section performs the cropping range control to return the cropping range to a state before the cropping range control is performed.

(7) The medical observation apparatus according to (6), in which
the control section performs the movement mechanism control to raise a movement velocity of the imaging field of view by the movement mechanism in correspondence with the cropping range control that returns the cropping range.

(8) The medical observation apparatus according to (6) or (7), in which
when the cropping range control that returns the cropping range is completed, the control section causes the imaging field of view to move by performing the movement mechanism control on the basis of the predetermined operation.

(9) The medical observation apparatus according to any one of (6) to (8), in which
when the cropping range control that returns the cropping range is completed, the control section stops execution of the cropping range control.

(10) The medical observation apparatus according to any one of (5) to (9), in which
in a case in which a stopping of the predetermined operation is detected after the cropping range control and the movement mechanism control are started, but before the movement of the imaging field of view by the movement mechanism is started,
the control section stops the execution of each of the cropping range control and the movement mechanism control.

(11) The medical observation apparatus according to (10), in which
in a case in which, when the stopping of the predetermined operation is detected, a movement amount of the imaging field of view by the cropping range control is equal to or greater than a set threshold value, or in a case in which the movement amount is greater than the threshold value,
the control section additionally performs the cropping range control to return the cropping range to a state before the cropping range control is performed, and in addition, performs the movement mechanism control so that a movement velocity of the imaging field of view becomes a movement velocity corresponding to the stopping of the predetermined operation.

(12) The medical observation apparatus according to (11), in which
when the cropping range control that returns the cropping range is completed, the control section stops the execution of each of the cropping range control and the movement mechanism control.

(13) The medical observation apparatus according to any one of (5) to (12), in which
in a case in which a stopping of the predetermined operation is detected after the movement of the imaging field of view by the movement mechanism is started, but before a movement velocity of the imaging field of view by the movement mechanism becomes a set target field of view movement velocity,
the control section performs each of the cropping range control and the movement mechanism control so that the movement velocity of the imaging field of view becomes a movement velocity corresponding to the stopping of the predetermined operation.

(14) The medical observation apparatus according to (13), in which
the control section performs the movement mechanism control so that the movement velocity of the imaging field of view by the movement mechanism falls, and in addition, performs the cropping range control so that the movement velocity of the imaging field of view becomes the movement velocity corresponding to the stopping of the predetermined operation.

(15) The medical observation apparatus according to (14), in which
in a case in which the movement velocity of the imaging field of view by the movement mechanism has become the movement velocity corresponding to the stopping of the predetermined operation,
the control section performs the cropping range control to return the cropping range to a state before the cropping range control is performed, and in addition, performs the movement mechanism control so that the movement velocity of the imaging field of view becomes the movement velocity corresponding to the stopping of the predetermined operation.

(16) The medical observation apparatus according to (15), in which when the cropping range control that returns the cropping range is completed, the control section stops the execution of each of the cropping range control and the movement mechanism control.

(17) The medical observation apparatus according to any one of (1) to (16), in which the controls section controls the movement of the imaging field of view so that a movement velocity of the imaging field of view is constant.

(18) The medical observation apparatus according to any one of (1) to (17), including:

the arm; and the imaging device supported by the arm.

(19) A control method executed by a medical observation apparatus, the method including:

controlling, on a basis of a predetermined operation related to a movement of an imaging field of view, the movement of the imaging field of view in an imaging device supported by an arm including a plurality of links joined to each other by joint sections, in which in the controlling, the movement of the imaging field of view is controlled by performing a cropping range control that crops an imaging range of the imaging device on the basis of the predetermined operation.

What is claimed is:

1. A medical observation apparatus comprising:

control circuitry configured to control, on a basis of a predetermined operation related to a movement of an imaging field of view, the movement of the imaging field of view in an imaging device supported by an arm including a plurality of links joined to each other by joint sections, wherein the control circuitry controls the movement of the imaging field of view by performing a cropping range control that crops an imaging range of the imaging device on the basis of the predetermined operation, the control circuitry causes the imaging field of view to move by the cropping range control by causing the cropping range inside the imaging range to change in correspondence with the predetermined operation, the control circuitry controls the movement of the imaging field of view by additionally performing a movement mechanism control that moves the arm to cause the imaging field of view to move, on the basis of the predetermined operation, the control circuitry sets a velocity of the movement of the imaging field by a combination including a velocity of the cropping range and a velocity of the movement by the movement mechanism control, and the controls circuitry controls the movement of the imaging field of view so that the velocity of the movement of the imaging field of view is constant when the velocity of the movement mechanism control is non-zero and changing, and the velocity of the cropping range is non-zero and changing.

2. The medical observation apparatus according to claim 1, wherein in a case in which the predetermined operation is detected, the control circuitry starts the cropping range control and the movement mechanism control.

3. The medical observation apparatus according to claim 2, wherein after the movement of the imaging field of view by the movement mechanism starts, the control circuitry performs the cropping range control to return the cropping range to a state before the cropping range control is performed.

4. The medical observation apparatus according to claim 3, wherein when the cropping range control that returns the cropping range is completed, the control circuitry causes the imaging field of view to move by performing the movement mechanism control on the basis of the predetermined operation.

5. The medical observation apparatus according to claim 3, wherein when the cropping range control that returns the cropping range is completed, the control circuitry stops execution of the cropping range control.

6. The medical observation apparatus according to claim 2, wherein in a case in which a stopping of the predetermined operation is detected after the cropping range control and the movement mechanism control are started, but before the movement of the imaging field of view by the movement mechanism is started, the control circuitry stops the execution of each of the cropping range control and the movement mechanism control.

7. The medical observation apparatus according to claim 6, wherein in a case in which, when the stopping of the predetermined operation is detected, a movement amount of the imaging field of view by the cropping range control is equal to or greater than a set threshold value, or in a case in which the movement amount is greater than the threshold value, the control circuitry additionally performs the cropping range control to return the cropping range to a state before the cropping range control is performed, and in addition, performs the movement mechanism control so that a movement velocity of the imaging field of view becomes a movement velocity corresponding to the stopping of the predetermined operation.

8. The medical observation apparatus according to claim 7, wherein when the cropping range control that returns the cropping range is completed, the control circuitry stops the execution of each of the cropping range control and the movement mechanism control.

9. The medical observation apparatus according to claim 2, wherein in a case in which a stopping of the predetermined operation is detected after the movement of the imaging field of view by the movement mechanism is started, but before a movement velocity of the imaging field of view by the movement mechanism becomes a set target field of view movement velocity, the control circuitry performs each of the cropping range control and the movement mechanism control so that the movement velocity of the imaging field of view becomes a movement velocity corresponding to the stopping of the predetermined operation.

10. The medical observation apparatus according to claim 9, wherein the control circuitry performs the movement mechanism control so that the movement velocity of the imaging field of view by the movement mechanism falls, and in addition, performs the cropping range control so that the movement velocity of the imaging field of view becomes the movement velocity corresponding to the stopping of the predetermined operation.

11. The medical observation apparatus according to claim 10, wherein
in a case in which the movement velocity of the imaging field of view by the movement mechanism has become the movement velocity corresponding to the stopping of the predetermined operation,
the control circuitry performs the cropping range control to return the cropping range to a state before the cropping range control is performed, and in addition, performs the movement mechanism control so that the movement velocity of the imaging field of view becomes the movement velocity corresponding to the stopping of the predetermined operation.

12. The medical observation apparatus according to claim 11, wherein
when the cropping range control that returns the cropping range is completed, the control circuitry stops the execution of each of the cropping range control and the movement mechanism control.

13. The medical observation apparatus according to claim 1, comprising:
the arm; and
the imaging device supported by the arm.

14. The medical observation apparatus according to claim 1, wherein
wherein the control circuitry initially causes a majority of the velocity of the movement of the imaging field by the moving of the cropping range, and subsequently causes the majority of the velocity of the movement by the movement mechanism control.

15. The medical observation apparatus according to claim 14, wherein
between when the control circuitry initially causes the majority of the velocity of the movement of the imaging field by the moving of the cropping range and when the control circuitry causes the majority of the velocity of the movement by the movement mechanism control, the control circuitry causes the velocity of the movement due to a substantial contribution by both the moving of the cropping range and the movement mechanism control.

16. The medical observation apparatus according to claim 1, wherein
during the movement of the imaging field, a size of objects in the imaging field is constant and a size of the cropping range is constant.

17. A medical observation apparatus comprising:
control circuitry configured to control, on a basis of a predetermined operation related to a movement of an imaging field of view, the movement of the imaging field of view in an imaging device supported by an arm including a plurality of links joined to each other by joint sections, wherein
the control circuitry controls the movement of the imaging field of view by performing a cropping range control that crops an imaging range of the imaging device on the basis of the predetermined operation,
the control circuitry controls the movement of the imaging field of view by additionally performing a movement mechanism control that moves the arm to cause the imaging field of view to move, on the basis of the predetermined operation,
in a case in which the predetermined operation is detected, the control circuitry starts the cropping range control and the movement mechanism control
after the movement of the imaging field of view by the movement mechanism starts, the control circuitry performs the cropping range control to return the cropping range to a state before the cropping range control is performed, and
the control circuitry performs the movement mechanism control to raise a movement velocity of the imaging field of view by the movement mechanism in correspondence with the cropping range control that returns the cropping range.

18. A control method executed by a medical observation apparatus, the method comprising:
controlling, on a basis of a predetermined operation related to a movement of an imaging field of view, the movement of the imaging field of view in an imaging device supported by an arm including a plurality of links joined to each other by joint sections, wherein
in the controlling, the movement of the imaging field of view is controlled by performing a cropping range control that crops an imaging range of the imaging device on the basis of the predetermined operation,
the controlling causes the imaging field of view to move by the cropping range control by causing the cropping range inside the imaging range to change in correspondence with the predetermined operation,
the controlling controls the movement of the imaging field of view by additionally performing a movement mechanism control that moves the arm to cause the imaging field of view to move, on the basis of the predetermined operation,
the controlling sets a velocity of the movement of the imaging field by a combination including a velocity of the cropping range and a velocity of the movement by the movement mechanism control, and
the controlling controls the movement of the imaging field of view so that the velocity of the movement of the imaging field of view is constant when the velocity of the movement mechanism control is non-zero and changing, and the velocity of the cropping range is non-zero and changing.

19. The control method according to claim 18, wherein
wherein the controlling initially causes a majority of the velocity of the movement of the imaging field by the moving of the cropping range, and subsequently causes the majority of the velocity of the movement by the movement mechanism control.

20. The control method according to claim 19, wherein between when the controlling causes the majority of the velocity of the movement of the imaging field by the moving of the cropping range and when the controlling causes the majority of the velocity of the movement by the movement mechanism control, the controlling causes the velocity of the movement due to a substantial contribution by both the moving of the cropping range and the movement mechanism control.

* * * * *